(12) United States Patent
Qiao et al.

(10) Patent No.: US 12,350,059 B2
(45) Date of Patent: Jul. 8, 2025

(54) ROBUST VENTRICULAR SENSING OF FAR-FIELD EGM OR ECG SIGNALS THAT AVOIDS OVERSENSING OF VENTRICULAR SENSED EVENTS

(71) Applicant: Pacesetter, Inc., Sylmar, CA (US)

(72) Inventors: Yun Qiao, Sunnyvale, CA (US); Nima Badie, Oakland, CA (US); Wenwen Li, Studio City, CA (US); Chaoyi Kang, Northridge, CA (US); Jan Mangual, Milan (IT); Fady Dawoud, Studio City, CA (US)

(73) Assignee: Pacesetter, Inc., Sylmar, CA (US)

( * ) Notice: Subject to any disclaimer, the term of this patent is extended or adjusted under 35 U.S.C. 154(b) by 403 days.

(21) Appl. No.: 17/745,260

(22) Filed: May 16, 2022

(65) Prior Publication Data
US 2023/0072043 A1 Mar. 9, 2023

Related U.S. Application Data

(60) Provisional application No. 63/241,466, filed on Sep. 7, 2021.

(51) Int. Cl.
*A61B 5/0245* (2006.01)
*A61B 5/00* (2006.01)
(Continued)

(52) U.S. Cl.
CPC ............ *A61B 5/352* (2021.01); *A61B 5/0245* (2013.01); *A61B 5/076* (2013.01); *A61B 5/287* (2021.01);
(Continued)

(58) Field of Classification Search
CPC ......... A61B 5/352; A61B 5/363; A61B 5/333; A61B 5/287; A61B 5/0245; A61B 5/686; A61B 5/7203; G16H 50/30
See application file for complete search history.

(56) References Cited

U.S. PATENT DOCUMENTS

| 5,755,739 A | 5/1998 | Sun et al. |
| 6,671,548 B1 | 12/2003 | Mouchawar et al. |

(Continued)

FOREIGN PATENT DOCUMENTS

| EP | 1549213 B1 | 8/2007 |
| EP | 1615693 B1 | 1/2011 |

(Continued)

OTHER PUBLICATIONS

Response to Extended European Search Report dated Apr. 13, 2023, European Patent Application No. 22169210.6.
(Continued)

*Primary Examiner* — Carl H Layno
*Assistant Examiner* — Aya Ziad Bakkar
(74) *Attorney, Agent, or Firm* — Pearl Cohen Zedek Latzer Baratz, LLP

(57) ABSTRACT

Described herein are methods, devices, and systems that identify ventricular sensed (VS) events from a signal indicative of cardiac electrical activity, such a far-field EGM or ECG signal, and monitor for an arrythmia and/or perform arrythmia discrimination based on the VS events. Beneficially, such embodiments reduce the probability of double-counting of R-wave, or more generally, of oversensing VS events, and thereby provide for improved arrythmia detection and arrythmia discrimination.

20 Claims, 11 Drawing Sheets

(51) Int. Cl.
  *A61B 5/07* (2006.01)
  *A61B 5/287* (2021.01)
  *A61B 5/333* (2021.01)
  *A61B 5/352* (2021.01)
  *A61B 5/363* (2021.01)
  *G16H 40/67* (2018.01)
  *G16H 50/30* (2018.01)

(52) U.S. Cl.
  CPC .............. *A61B 5/333* (2021.01); *A61B 5/363* (2021.01); *A61B 5/686* (2013.01); *A61B 5/7203* (2013.01); *G16H 40/67* (2018.01); *G16H 50/30* (2018.01)

(56) References Cited

U.S. PATENT DOCUMENTS

| | | |
|---|---|---|
| 7,027,858 B2 | 4/2006 | Cao et al. |
| 7,155,282 B1 | 12/2006 | Min et al. |
| 7,167,747 B2 | 1/2007 | Gunderson et al. |
| 7,218,966 B2 | 5/2007 | Haefner |
| 7,266,409 B2 | 9/2007 | Gunderson |
| 7,283,863 B2 | 10/2007 | Gunderson et al. |
| 7,333,855 B2 | 2/2008 | Gunderson et al. |
| 7,412,282 B2 | 8/2008 | Houben |
| 7,537,569 B2 | 5/2009 | Sarkar et al. |
| 7,567,835 B2 | 7/2009 | Gunderson et al. |
| 7,582,061 B2 | 9/2009 | Li et al. |
| 7,623,911 B2 | 11/2009 | Sarkar et al. |
| 7,630,756 B2 | 12/2009 | Linker |
| 7,634,310 B2 | 12/2009 | Lee et al. |
| 7,774,049 B2 | 8/2010 | Ghanem et al. |
| 7,774,062 B2 | 8/2010 | Kim et al. |
| 7,783,354 B2 | 8/2010 | Gunderson |
| 7,818,056 B2 | 10/2010 | Kim et al. |
| 7,831,301 B2 | 11/2010 | Webb et al. |
| 7,894,893 B2 | 2/2011 | Kim et al. |
| 7,912,545 B2 | 3/2011 | Li et al. |
| 8,078,277 B2 | 12/2011 | Gunderson et al. |
| 8,160,686 B2 | 4/2012 | Allavatam et al. |
| 8,260,404 B1 | 9/2012 | Bharmi et al. |
| 8,265,737 B2 | 9/2012 | Warren et al. |
| 8,265,756 B1 * | 9/2012 | Snell .................. A61N 1/36507 600/509 |
| 8,386,024 B2 | 2/2013 | Gunderson et al. |
| 8,406,872 B2 | 3/2013 | Stadler et al. |
| 8,437,840 B2 | 5/2013 | Patel et al. |
| 8,437,851 B2 | 5/2013 | Corbucci et al. |
| 8,473,042 B2 | 6/2013 | McCarthy et al. |
| 8,506,500 B2 | 8/2013 | Li et al. |
| 8,521,281 B2 | 8/2013 | Patel et al. |
| 8,538,524 B2 | 9/2013 | Rosenberg et al. |
| 8,560,058 B2 | 10/2013 | Babaeizadeh et al. |
| 8,560,069 B2 | 10/2013 | Zhang |
| 8,577,455 B2 | 11/2013 | Mitrani et al. |
| 8,583,221 B1 | 11/2013 | Patel et al. |
| 8,588,895 B2 | 11/2013 | Sanghera et al. |
| 8,588,896 B2 | 11/2013 | Allavatam et al. |
| 8,600,490 B1 * | 12/2013 | Bharmi ................ A61N 1/0563 607/9 |
| 8,626,280 B2 | 1/2014 | Allavatam et al. |
| 8,639,316 B2 | 1/2014 | Sarkar |
| 8,744,559 B2 | 6/2014 | Houben et al. |
| 8,750,994 B2 | 6/2014 | Ghosh et al. |
| 8,774,909 B2 | 7/2014 | Patel |
| 8,781,585 B2 | 7/2014 | Gunderson et al. |
| 8,792,971 B2 | 7/2014 | Gunderson et al. |
| 8,886,296 B2 | 11/2014 | Patel |
| 8,897,863 B2 | 11/2014 | Linker |
| 8,914,106 B2 | 12/2014 | Charlton et al. |
| 8,942,793 B2 | 1/2015 | Eberle et al. |
| 9,101,278 B2 | 8/2015 | Fischell et al. |
| 9,167,747 B1 | 10/2015 | Andros et al. |
| 9,307,920 B2 | 4/2016 | Mahajan et al. |
| 9,314,210 B2 | 4/2016 | Li |
| 9,339,662 B2 | 5/2016 | Allavatam et al. |
| 9,381,370 B2 | 7/2016 | Gunderson |
| 9,468,766 B2 | 10/2016 | Sheldon et al. |
| 9,522,283 B2 | 12/2016 | Bardy et al. |
| 9,597,525 B2 | 3/2017 | Cao et al. |
| 9,675,261 B2 | 6/2017 | Cao et al. |
| 9,682,238 B2 | 6/2017 | Zhang et al. |
| 9,724,007 B2 | 8/2017 | Cole |
| 9,962,100 B2 | 5/2018 | Allavatam et al. |
| 9,993,653 B2 | 6/2018 | Bardy et al. |
| 9,999,368 B2 | 6/2018 | Perschbacher et al. |
| 10,004,418 B2 | 6/2018 | Cao et al. |
| 10,183,171 B2 | 1/2019 | Ostroff et al. |
| 10,328,274 B2 | 6/2019 | Zhang et al. |
| 10,548,499 B2 | 2/2020 | Bayasi et al. |
| 10,576,288 B2 | 3/2020 | Cao et al. |
| 10,582,870 B2 | 3/2020 | Allavatam et al. |
| 10,702,180 B2 | 7/2020 | Perschbacher et al. |
| 10,709,379 B2 | 7/2020 | Warren et al. |
| 2003/0204215 A1 | 10/2003 | Gunderson et al. |
| 2006/0224075 A1 | 10/2006 | Gunderson et al. |
| 2007/0232948 A1 | 10/2007 | Stadler et al. |
| 2008/0161870 A1 | 7/2008 | Gunderson |
| 2010/0280567 A1 | 11/2010 | Gunderson |
| 2015/0045682 A1 | 2/2015 | Sanghera et al. |
| 2017/0354827 A1 | 12/2017 | Zhang et al. |
| 2018/0264258 A1 | 9/2018 | Cheng et al. |
| 2018/0311504 A1 | 11/2018 | Cao et al. |
| 2018/0318588 A1 | 11/2018 | Dennis |
| 2019/0329038 A1 | 10/2019 | Rhude |
| 2020/0100694 A1 | 4/2020 | Sarkar et al. |
| 2021/0038905 A1 | 2/2021 | Cao et al. |
| 2021/0076964 A1 | 3/2021 | Mahajan et al. |
| 2021/0170170 A1 | 6/2021 | Mischler et al. |
| 2021/0236041 A1 | 8/2021 | Badie et al. |
| 2021/0369175 A1 | 12/2021 | Badie et al. |

FOREIGN PATENT DOCUMENTS

| | | |
|---|---|---|
| EP | 2079520 B1 | 11/2013 |
| EP | 1877137 B1 | 10/2014 |
| EP | 2967402 B1 | 1/2016 |
| EP | 2364107 B1 | 9/2016 |
| EP | 1219237 B1 | 2/2017 |
| EP | 3247453 B1 | 11/2017 |
| EP | 2895063 B1 | 1/2019 |
| EP | 3422934 B1 | 1/2019 |
| EP | 3432774 B1 | 1/2019 |
| EP | 3566746 A1 | 5/2019 |
| EP | 3592419 B1 | 1/2020 |
| EP | 2741662 B1 | 3/2021 |
| WO | WO2003/092810 A2 | 11/2003 |
| WO | WO2019/075529 A1 | 4/2019 |
| WO | WO-2021007518 A1 * | 1/2021 ........... A61H 31/005 |

OTHER PUBLICATIONS

Extended European Search Report dated Sep. 9, 2022, European Patent Application No. 22169210.6.

Hadjileontiadis, Leontios J., et al., "Performance of Three QRS Detection Algorithms During Sleep: A Comparative Study," 2001 Proceedings of the 23rd Annual EMBS International Conference, Oct. 25-28, 2001, 4 pages.

Pandit, Diptangshu, et al., "A lightweight QRS detector for single lead ECG signals using a max-min difference algorithm," Computer Methods and Programs in Biomedicine, 144, Feb. 2017 15 pages.

Extended European Search Report dated Oct. 19, 2021, European Patent Application No. 21170198.2-1132.

Response to Extended European Search Report dated Feb. 4, 2022, European Patent Application No. 21170198.2-1132.

International Search Report & The Written Opinion of the International Searching Authority dated Mar. 31, 2021, International Application No. PCT/US2021/014332.

"Spontaneous T-wave oversensing," Cardiocases, Pacing & Defibrillation, [https://www.cardiocases.com/en/pacingdefibrillation/clinical-situation/icd/spontaneous-t-wave-oversensing], downloaded Jun. 1, 2021, 9 pages.

(56) References Cited

OTHER PUBLICATIONS

U.S. Appl. No. 17/723,207, filed Apr. 18, 2022.
Communication under Rule 71(3) EPC dated Dec. 4, 2024, European Application No. 22169210.6-1113.
Non-final Office Action dated Feb. 6, 2025, U.S. Appl. No. 17/723,207, filed Apr. 18, 2022.

* cited by examiner ical activity, and monitor for an arrythmia and/or perform arrythmia discrimination based on the VS events.

ROBUST VENTRICULAR SENSING OF FAR-FIELD EGM OR ECG SIGNALS THAT AVOIDS OVERSENSING OF VENTRICULAR SENSED EVENTS

PRIORITY CLAIM

This application claims priority to U.S. Provisional Patent Application No. 63/241,466, filed Sep. 7, 2021, which is incorporated herein by reference.

FIELD

Embodiments described herein relate to methods, devices, and systems that identify ventricular sensed (VS) events from a signal indicative of cardiac electrical activity, such a far-field electrocardiogram (EGM), and monitor for an arrythmia and/or perform arrythmia discrimination based on the VS events.

BACKGROUND

Implantable medical devices (IMDs), such as implantable cardioverter/defibrillator devices (ICDs) and insertable cardiac monitors (ICMs), are well known in the art. Such devices can be used, e.g., to detect ventricular fibrillation (VF) and ventricular tachycardia (VT), and where the IMD is capable of performing therapy, the IMD may deliver defibrillating electrical energy, cardioversion shocks or anti-tachycardia pacing (ATP) pulses to the heart when ventricular fibrillation (VF) or ventricular tachycardia (VT) is detected.

One problem that must be addressed in such IMDs is the need to reliably sense R-waves, or more generally, the need to reliably detect ventricular sensed (VS) events. To this end, IMDs often utilize some type of automatic sensing control. The aim of such control is to maintain an R-wave sensing threshold low enough (sensitive enough) for detecting low amplitude R-wave electrical activity of the heart (as may be present during fibrillation) while avoiding over-sensing which could result in T-waves and/or noise being sensed by the IMD and mistaken for R-waves. Where a T-wave is mistaken for an R-wave, that is known as T-wave oversensing (TWO).

Some IMDs perform bipolar sensing of a near-field cardiac signal, which can also be a near-field electrocardiogram (EGM) signal. Such an IMD may rectify the near-field EGM signal to produce a rectified EGM signal that is compared to a dynamic sensing threshold. An example method and device for utilizing and adjusting such a dynamic sensing threshold is disclosed in U.S. Pat. No. 7,155,282 to Min et al., titled "Automatic Sensitivity Control and Method for Use in an Implantable Cardiac Stimulation Device," which is incorporated herein by reference.

Other IMDs, such as non-vascular ICDs (NV-ICDs) and ICMs, may utilize spaced apart electrodes outside the heart to sense far-field EGM signals or a far-field electrogram (EGM) signals, instead of sensing near-field EGM signals. These far-field signals may be wide and complex in morphology during some rhythms, such as VT, VF and rate-dependent bundle branch block. In such cases, signal rectification often results in double-counting of R-wave, or more generally, R-wave oversensing.

A number of recent case studies have reported that R-wave oversensing during VT in some patients having a subcutaneous ICD (S-ICD), which is a type of NV-ICD, have led to inappropriate shocks being delivered to the patients. More specifically, R-wave oversensing during slow VT, with a ventricular rate below the programmed VT cutoff rate, caused shock delivery to many patients. In some patients this led to the S-ICD being explanted and replaced with a transvenous ICD.

In view of the above, is can be appreciated that there is still a need for improving the detection of R-waves, or more generally, improving the detection of ventricular sensed (VS) events, especially where the sensed signal being used to detect VS events is a far-field signal.

SUMMARY

Certain embodiments of the present technology relate to methods, devices and systems that identify ventricular sensed (VS) events from a signal indicative of cardiac electrical activity, and monitor for an arrythmia and/or perform arrythmia discrimination based on the VS events. The signal indicative of cardiac electrical activity can be, e.g., a non-rectified far-field electrogram (EGM) signal or a non-rectified far-field electrocardiogram (ECG) signal.

In accordance with certain embodiments, a method includes detecting when positive portions of the signal indicative of cardiac electrical activity cross a first dynamic sensing threshold to thereby detect first threshold crossings, each of which is indicative of a detected potential VS event. The method also includes detecting when negative portions of the signal indicative of cardiac electrical activity cross a second dynamic sensing threshold to thereby detect second threshold crossings, each of which is indicative of a detected potential VS event. The method also includes starting a positive signal refractory period in response to each first threshold crossing, and ending each positive signal refractory period after a first specified interval has elapsed. The method further includes starting a negative signal refractory period in response to each second threshold crossing, and ending each negative signal refractory period after a second specified interval has elapsed. The method also includes starting a shared signal refractory period in response to each first threshold crossing that occurs outside of the positive and the shared signal refractory periods, and starting a shared signal refractory period in response to each second threshold crossing that occurs outside of the negative and the shared signal refractory periods. Additionally the method includes rejecting each potential VS event that was detected within a shared signal refractory period, and using the detected potential VS events, that were not rejected, to monitor for an arrythmia and/or perform arrythmia discrimination.

In accordance with certain embodiments, the method further includes, for each shared signal refractory period that is started in response to a first threshold crossing occurring outside of the positive and the shared signal refractory periods, ending the shared signal refractory period after a third specified interval has elapsed or in response to a second threshold crossing occurring, whichever occurs first. Such a method further includes, for each shared signal refractory period that is started in response to a second threshold crossing occurring outside of the negative and the shared signal refractory periods, ending the shared signal refractory period after the third specified interval has elapsed or in response to a first threshold crossing occurring, whichever occurs first.

In accordance with certain embodiments, the second specified interval has a same duration as the first specified interval, and the third specified interval has a greater duration than each of the first and the second specified intervals.

For example, the third specified interval can have a duration that is 1.5 times the duration of the first and second intervals.

In accordance with certain embodiments, detecting when negative portions of the signal indicative of cardiac electrical activity cross the second dynamic sensing threshold, includes inverting the signal indicative of cardiac electrical activity to produce an inverted version of the signal indicative of cardiac electrical activity and comparing the inverted version of the signal indicative of cardiac electrical activity to the second dynamic sensing threshold to thereby detect second threshold crossings, each of which is indicative of a detected potential VS event.

In accordance with certain embodiments, the method further includes separately adjusting the first dynamic sensing threshold and the second dynamic sensing threshold, such that the first dynamic sensing threshold is adjusted based on peaks in the signal indicative of cardiac electrical activity that are detected within the positive signal refractory periods, and the second dynamic sensing threshold is adjusted based on peaks in the signal indicative of cardiac electrical activity that are detected within the negative signal refractory periods. More specifically, in accordance with certain embodiments the adjusting the first dynamic sensing threshold includes setting a magnitude of the first dynamic sensing threshold, following a positive signal refractory period, to a specified percent of a peak in the signal indicative of cardiac electrical activity that is detected within the positive signal refractory period, and after an optional decay delay period, gradually decreasing the magnitude of the first dynamic sensing threshold in accordance with a specified decay rate until the first dynamic sensing threshold reaches a specified minimum magnitude or another first threshold crossing occurs, whichever occurs first. Similarly, in accordance with certain embodiments, adjusting the second dynamic sensing threshold includes setting a magnitude of the second dynamic sensing threshold, following a negative signal refractory period, to the specified percent of a peak in the signal indicative of cardiac electrical activity that is detected within the negative signal refractory period, and after the optional decay delay period, gradually decreasing the magnitude of the second dynamic sensing threshold in accordance with the specified decay rate until the second dynamic sensing threshold reaches the specified minimum magnitude or another second threshold crossing occurs, whichever occurs first.

In accordance with certain embodiments, using the detected potential VS events, that were not rejected, to monitor for an arrythmia and/or perform arrythmia discrimination comprises at least one of the following: monitoring for a ventricular arrhythmia based on a rate of the detected potential VS events that were not rejected; monitoring for a ventricular arrhythmia based on durations of intervals between the detected potential VS events that were not rejected; monitoring for a ventricular arrhythmia based on a variability of intervals between the detected potential VS events that were not rejected; or discriminating between ventricular tachycardia (VT) and ventricular fibrillation (VF) based on the detected potential VS events that were not rejected.

An apparatus according to certain embodiments of the present technology includes two or more electrodes, a sensing circuit coupleable to at least two of the electrodes to thereby sense a signal indicative of cardiac electrical activity, and at least one processor. In accordance with certain embodiments, the apparatus comprises an implantable medical device (IMD) and the signal indicative of cardiac electrical activity comprises a non-rectified far-field EGM signal or a non-rectified far-field ECG signal. The at least one processor is configured to detect when positive portions of the signal indicative of cardiac electrical activity cross a first dynamic sensing threshold to thereby detect first threshold crossings, each of which is indicative of a detected potential VS event. The at least one processor is also configured to detect when negative portions of the signal indicative of cardiac electrical activity cross a second dynamic sensing threshold to thereby detect second threshold crossings, each of which is indicative of a detected potential VS event. Additionally, the at least one processor is configured to start a positive signal refractory period in response to each first threshold crossing, and end each positive signal refractory period after a first specified interval has elapsed. The at least one processor is also configured start a negative signal refractory period in response to each second threshold crossing, and end each negative signal refractory period after a second specified interval has elapsed. Further, the at least one processor is configured to start a shared signal refractory period in response to each first threshold crossing that occurs outside of the positive and the shared signal refractory periods, and start a shared signal refractory period in response to each second threshold crossing that occurs outside of the negative and the shared signal refractory periods. Additionally, the at least one processor is configured to reject each potential VS event that was detected within a shared signal refractory period, and use the detected potential VS events, that were not rejected, to monitor for an arrythmia and/or perform arrythmia discrimination.

In accordance with certain embodiments, the at least one processor is further configured to: for each shared signal refractory period that is started in response to a first threshold crossing occurring outside of the positive and the shared signal refractory periods, end the shared signal refractory period after a third specified interval has elapsed or in response to a second threshold crossing occurring, whichever occurs first; and for each shared signal refractory period that is started in response to a second threshold crossing occurring outside of the negative and the shared signal refractory periods, end the shared signal refractory period after the third specified interval has elapsed or in response to a first threshold crossing occurring, whichever occurs first.

In accordance with certain embodiments, the second specified interval has a same duration as the first specified interval, and the third specified interval has a greater duration than each of the first and the second specified intervals.

In accordance with certain embodiments, the at least one processor is configured to detect when negative portions of the signal indicative of cardiac electrical activity cross the second dynamic sensing threshold, by producing an inverted version of the signal indicative of cardiac electrical activity and comparing the inverted version of the signal indicative of cardiac electrical activity to the second dynamic sensing threshold to thereby detect second threshold crossings, each of which is indicative of a detected potential VS event.

In accordance with certain embodiments, the at least one processor is further configured to separately adjust the first dynamic sensing threshold and the second dynamic sensing threshold, such that the first dynamic sensing threshold is adjusted based on peaks in the signal indicative of cardiac electrical activity that are detected within the positive signal refractory periods, and the second dynamic sensing threshold is adjusted based on peaks in the signal indicative of cardiac electrical activity that are detected within the negative signal refractory periods.

In accordance with certain embodiments, the at least one processor is configured to adjust the first dynamic sensing threshold by setting a magnitude of the first dynamic sensing threshold, following a positive signal refractory period, to a specified percent of a peak in the signal indicative of cardiac electrical activity that is detected within the positive signal refractory period, and after an optional decay delay period, gradually decreasing the magnitude of the first dynamic sensing threshold in accordance with a specified decay rate until the first dynamic sensing threshold reaches a specified minimum magnitude or another first threshold crossing occurs, whichever occurs first. The at least one processor is further configured to adjust the second dynamic sensing threshold by setting a magnitude of the second dynamic sensing threshold, following a negative signal refractory period, to the specified percent of a peak in the signal indicative of cardiac electrical activity that is detected within the negative signal refractory period, and after the optional decay delay period, gradually decreasing the magnitude of the second dynamic sensing threshold in accordance with the specified decay rate until the second dynamic sensing threshold reaches the specified minimum magnitude or another second threshold crossing occurs, whichever occurs first.

In accordance with certain embodiments, the at least one processor is configured to at least one of: monitor for a ventricular arrhythmia based on a rate of the detected potential VS events that were not rejected; monitor for a ventricular arrhythmia based on durations of intervals between the detected potential VS events that were not rejected; monitor for a ventricular arrhythmia based on a variability of intervals between the detected potential VS events that were not rejected; or discriminate between VT and VF based on the detected potential VS events that were not rejected.

In accordance with certain embodiments, a method comprises: comparing a non-rectified far-field ECG or EGM signal to a first dynamic sensing threshold and to a second dynamic sensing threshold to thereby detect first threshold crossings and second threshold crossings, each of which is indicative of a detected potential VS event; initiating a positive signal refractory period in response to each first threshold crossing, and initiating a negative signal refractory period in response to each second threshold crossing; initiating a shared signal refractory period in response to each first threshold crossing that occurs outside of the positive and the shared signal refractory periods, and in response to each second threshold crossing that occurs outside of the negative and the shared signal refractory periods; and monitoring for an arrythmia and/or performing arrythmia discrimination based on the detected potential VS events that were detected outside of the positive, the negative and the shared signal refractory periods.

In accordance with certain such embodiments, the comparing the non-rectified far-field ECG or EGM signal to the second dynamic sensing threshold includes inverting the non-rectified far-field ECG or EGM signal to produce an inverted version the non-rectified far-field ECG or EGM signal, which is compared to the second dynamic sensing threshold.

In accordance with certain such embodiments, the method further comprises separately adjusting the first dynamic sensing threshold and the second dynamic sensing threshold.

In accordance with certain such embodiments, the method further comprises for each signal refractory period of the positive and the negative signal refractory periods, ending the signal refractory period a specified duration after being initiated. The method also comprises, for each shared signal refractory period that was initiated in response to a first threshold crossing occurring outside of the positive and the shared signal refractory periods, ending the shared signal refractory period after a further specified interval has elapsed or in response to a second threshold crossing occurring, whichever occurs first. The method also comprises, for each shared signal refractory period that was initiated in response to a second threshold crossing occurring outside of the negative and the shared signal refractory periods, ending the shared signal refractory period after the further specified interval has elapsed or in response to a first threshold crossing occurring, whichever occurs first.

This summary is not intended to be a complete description of the embodiments of the present technology. Other features and advantages of the embodiments of the present technology will appear from the following description in which the preferred embodiments have been set forth in detail, in conjunction with the accompanying drawings and claims.

BRIEF DESCRIPTION OF THE DRAWINGS

Embodiments of the present technology relating to both structure and method of operation may best be understood by referring to the following description and accompanying drawings, in which similar reference characters denote similar elements throughout the several views.

DETAILED DESCRIPTION

Certain embodiments of the present technology related to methods and devices that provide for robust R-wave sensing on a far-field cardiac signal, such as a far-field EGM or ECG signal. Such signals can be referred to collectively as an EGM/ECG signal, or more generally, as a signal indicative of cardiac electrical activity. Such embodiments analyze both positive and negative portions of a non-rectified far-field EGM/ECG signal, rather than analyzing a rectified EGM/ECG signal, to reduce the chance of R-waves being double counted, and more generally, to reduce the chance of oversensing of VS events.

Figure 1:
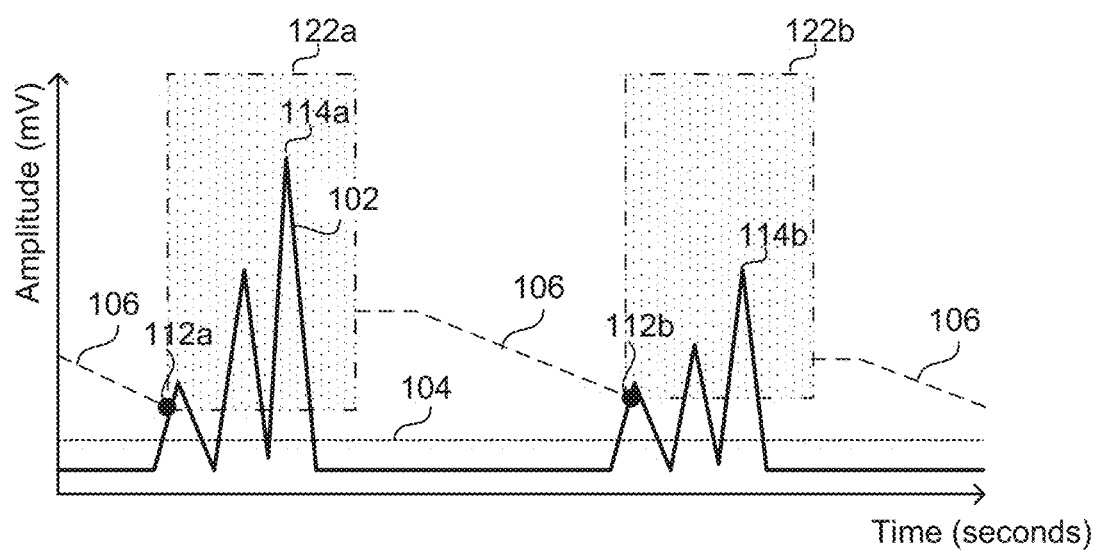
FIG. 1 illustrates an example of a rectified near-field EGM signal and is used to explain how a dynamic sensing threshold has been used to detect R-waves within a rectified near-field EGM signal.

Before providing further details of the embodiments of the present technology, FIG. 1 will first be used to provide additional details as to how a dynamic sensing threshold has been used to detect R-waves within a rectified EGM signal. Referring to FIG. 1, the solid line 102 illustrates an example rectified EGM signal, the dotted line 104 illustrates an example programmed maximum sensitivity level, and the dashed line 106 illustrates an example dynamic sensing threshold. Still referring to FIG. 1, the rectified EGM signal 102 is compared to the dynamic sensing threshold 106 such that an R-wave is sensed when the rectified EGM signal 102 crosses the dynamic sensing threshold 106, as indicated by the dot 112a. This starts a sense refractory period 122a, during which the rectified EGM signal 102 is not compared to the dynamic sensing threshold 106, and during which a peak 114a of the rectified EGM signal 102 within the sense refractory period 122a is identified, wherein the peak 114a is the peak R-wave amplitude. At the end of the sense refractory period 122a, the dynamic sensing threshold 106 is set to a programmed percentage (e.g., 62.5%) of the peak R-wave amplitude. For an example, if the peak R-wave amplitude is 7 millivolts (mV), then the dynamic sensing threshold 106 will be set to 3.75 mV at the end of the sense refractory period 122a. The dynamic sensing threshold 106 will then remain at that amplitude (i.e., at 3.75 mV in this example) for a programmed decay delay (e.g., 60 milliseconds (msec)) before beginning to decay at a programmed decay rate (e.g., 1 mV per second) until reaching the maximum sensitivity level 104. In this example the maximum sensitivity level 104 is the same as the minimum magnitude of the dynamic sensing threshold 106.

Still referring to FIG. 1, the rectified EGM signal 102 is shown as crossing the dynamic sensing threshold 106 again, as indicated by the dot 112b, which corresponds to another R-wave being sensed. This starts another sense refractory period 122b, during which the rectified EGM signal 102 is not compared to the dynamic sensing threshold 106, and during which a peak 114b of the rectified EGM signal 102 within the sense refractory period 122 is identified, wherein the peak 114b is another peak R-wave amplitude. At the end of the sense refractory period 122b, the dynamic sensing threshold 106 is set to a programmed percentage (e.g., 62.5%) of the peak R-wave amplitude. For an example, if the peak R-wave amplitude is 4 millivolts (mV), then the dynamic sensing threshold 106 will be set to 2.5 mV at the end of the sense refractory period 122b. The dynamic sensing threshold 106 will then remain at that amplitude (i.e., at 2.5 mV in this example) for the programmed decay delay (e.g., 60 ms) before beginning to decay at the programmed decay rate. It is possible that the programmed decay delay is set to zero, and thus, the decay delay can be considered optional.

Figure 2:
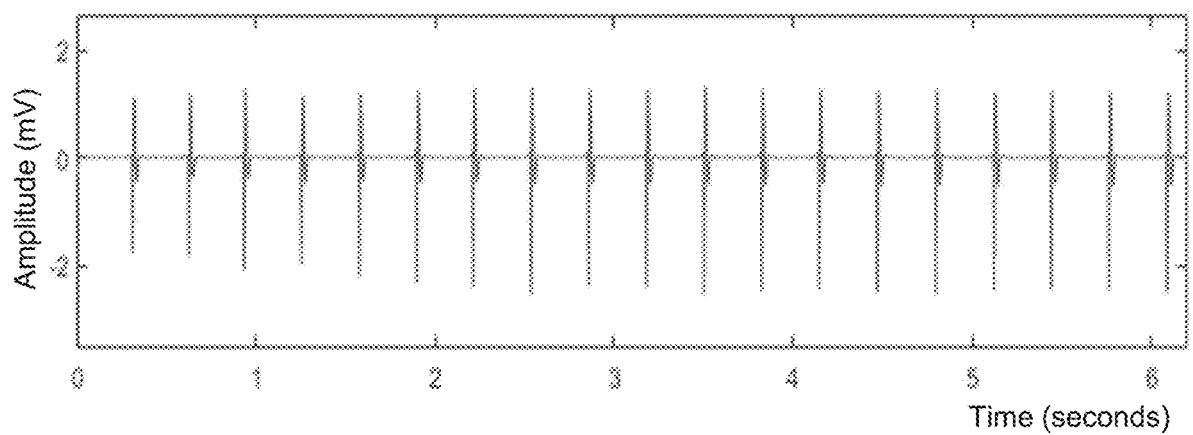
FIG. 2 illustrates an example of a near-field EGM signal during VT or VF.
Figure 3:
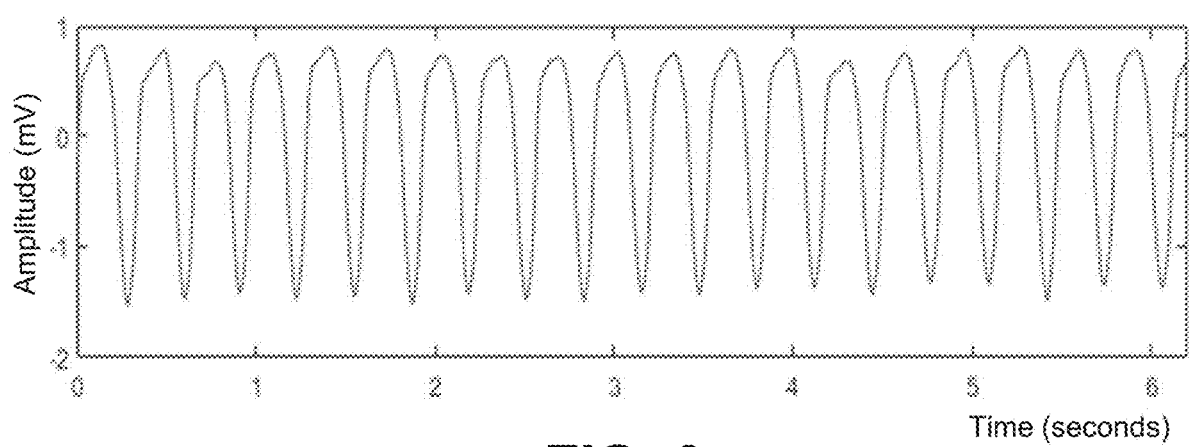
FIG. 3 illustrates an example of a far-field EGM signal during VT or VF.

One of the reasons the technique summarized above with reference to FIG. 1 works well when used with rectified near-field EGM signals is due to the relative narrow morphological features that are within near-field EGM signals. An example of how narrow the morphological features are within a near-field EGM signal 202 during ventricular tachycardia (VT) or ventricular fibrillation (VF) can be appreciated from FIG. 2. By contrast, far-field EGM signals have relatively wide morphological features. An example of how wide the morphological features are within a far-field EGM signal 302 during VT or VF can be appreciated from FIG. 3. Because of these aforementioned characteristics of a far-field EGM signal, signal rectification of a far-field EGM signal and then comparison of the rectified far-field EGM signal to a dynamic sensing threshold (similar to the dynamic sensing threshold 106 described above with reference to FIG. 1) often results in double-counting of R-wave, or more generally, R-wave oversensing.

Figure 4A:
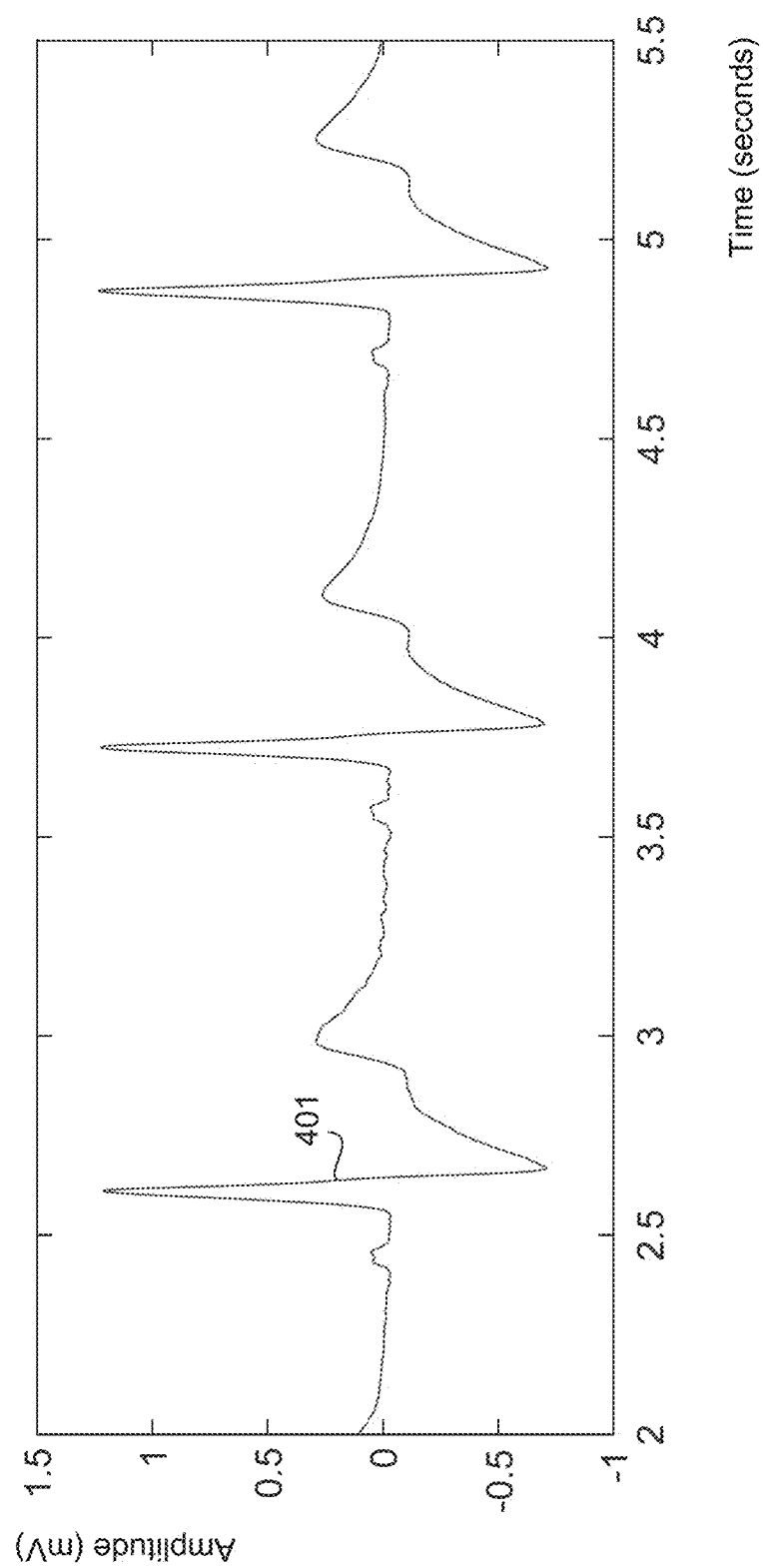
FIG. 4A illustrates an example of a far-field EGM signal during NSR.
Figure 4B:
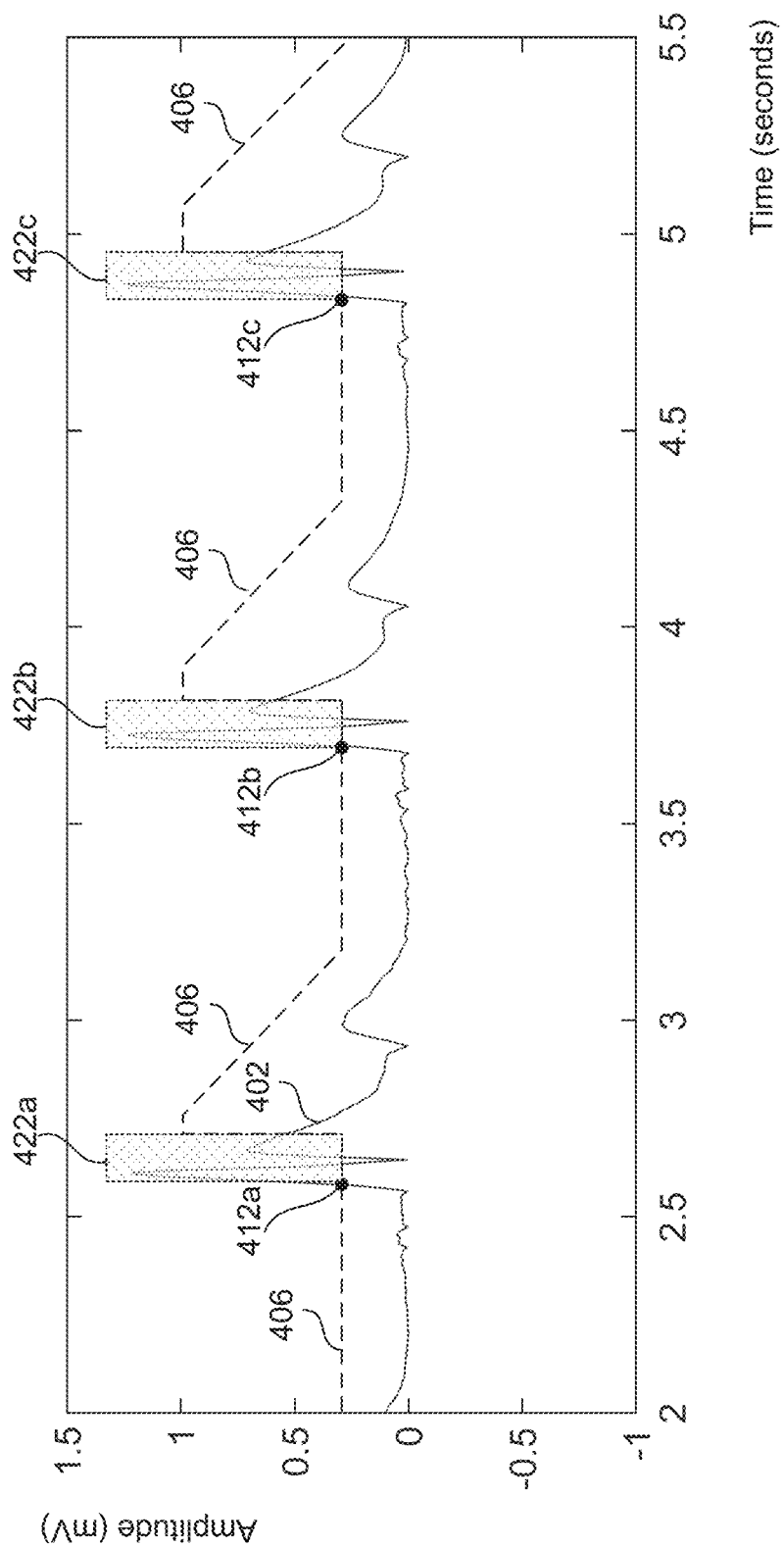
FIG. 4B illustrates a rectified version of the far-field EGM signal shown in FIG. 4A, and is used to explain how a dynamic sensing threshold can be used to detect potential VS events from the rectified far-field EGM signal.

FIG. 4A illustrates an example far-field EGM/ECG signal 401 sensed during normal sinus rhythm (NSR), where the far-field EGM/ECG signal 401 has not been rectified. FIG. 4B illustrates an example rectified far-field EGM/ECG signal 402 that is a rectified version of the far-field EGM/ECG signal 401 shown in FIG. 4A, which as noted above was sensed during NSR. Also shown in FIG. 4B is an example dynamic sensing threshold 406. The threshold crossings 412a, 412b, and 412c are each indictive a detected potential VS event. Also shown in FIG. 4B are sense refractory periods 422a, 422b, and 422c that are started (aka triggered or initiated), respectively, in response to the threshold crossings 412a, 412b, and 412c. In FIG. 4B, none of the R-waves in the rectified signal 402 were double counted.

Figure 5A:
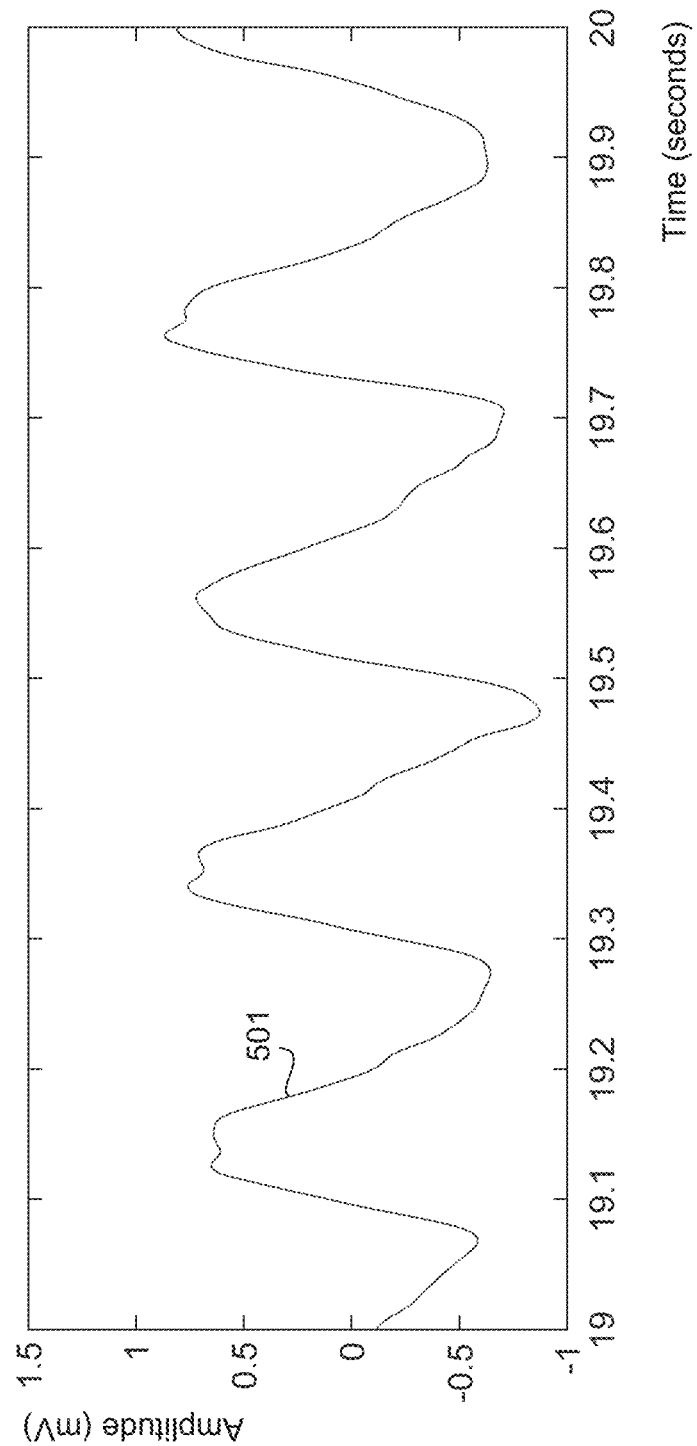
FIG. 5A illustrates an example of a far-field EGM signal during VT or VF.
Figure 5B:
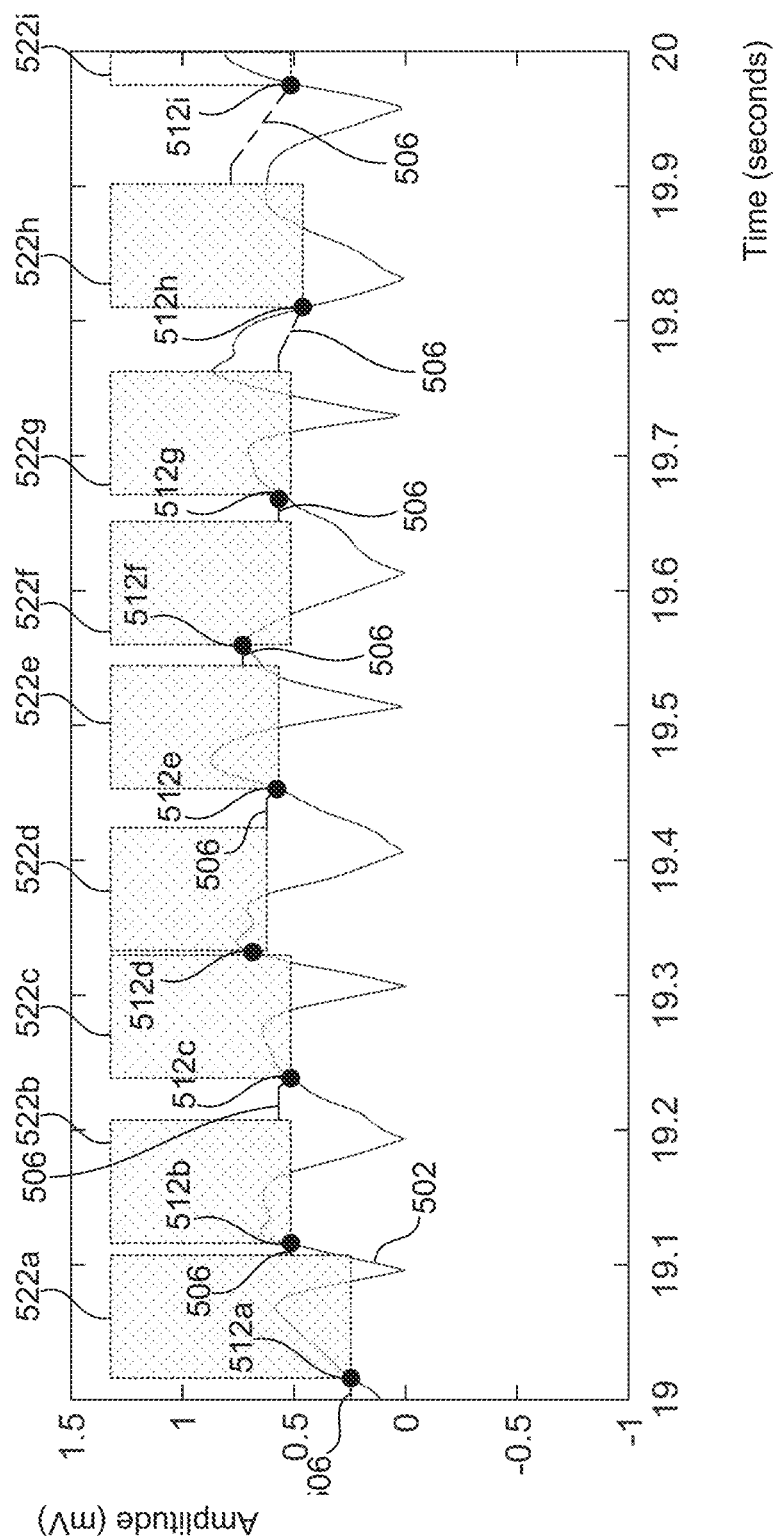
FIG. 5B illustrates a rectified version of the far-field EGM signal shown in FIG. 5A, and is used to explain how R-waves can be double-counted when using a dynamic sensing threshold to detect potential VS events from the rectified far-field EGM signal.

FIG. 5A illustrates an example far-field EGM/ECG signal 501 sensed during ventricular fibrillation (VF), where with far-field EGM/ECG signal 501 has not been rectified. FIG. 5B illustrates an example rectified far-field EGM/ECG signal 502 that is a rectified version of the far-field EGM/ECG signal 501 shown in FIG. 5A, which as noted above was sensed during VF. Also shown in FIG. 5B is an example dynamic sensing threshold 506. The threshold crossings 512a, 512b, 512c, 512d, 512e, 512f, 512g, 512h, and 512i are each indictive a detected potential VS event. Also shown in FIG. 5B are sense refractory periods 522a, 522b, 522c, 522d, 522e, 522f, 522g, 522h, and 522i that are started (aka triggered or initiated), respectively, in response to the threshold crossings 512a, 512b, 512c, 512d, 512e, 512f, 512g, 512h, and 512i. In FIG. 5B, the R-waves in the rectified signal 502 are shown as being double counted, because each of the R-waves in the rectified signal 502 causes two threshold crossings.

As noted above, and will be described in further detail below, certain embodiments of the present technology analyze both positive and negative portions of a non-rectified far-field EGM/ECG signal, rather than analyzing a rectified EGM/ECG signal, to reduce the chance of R-waves being double counted.

Figure 6:
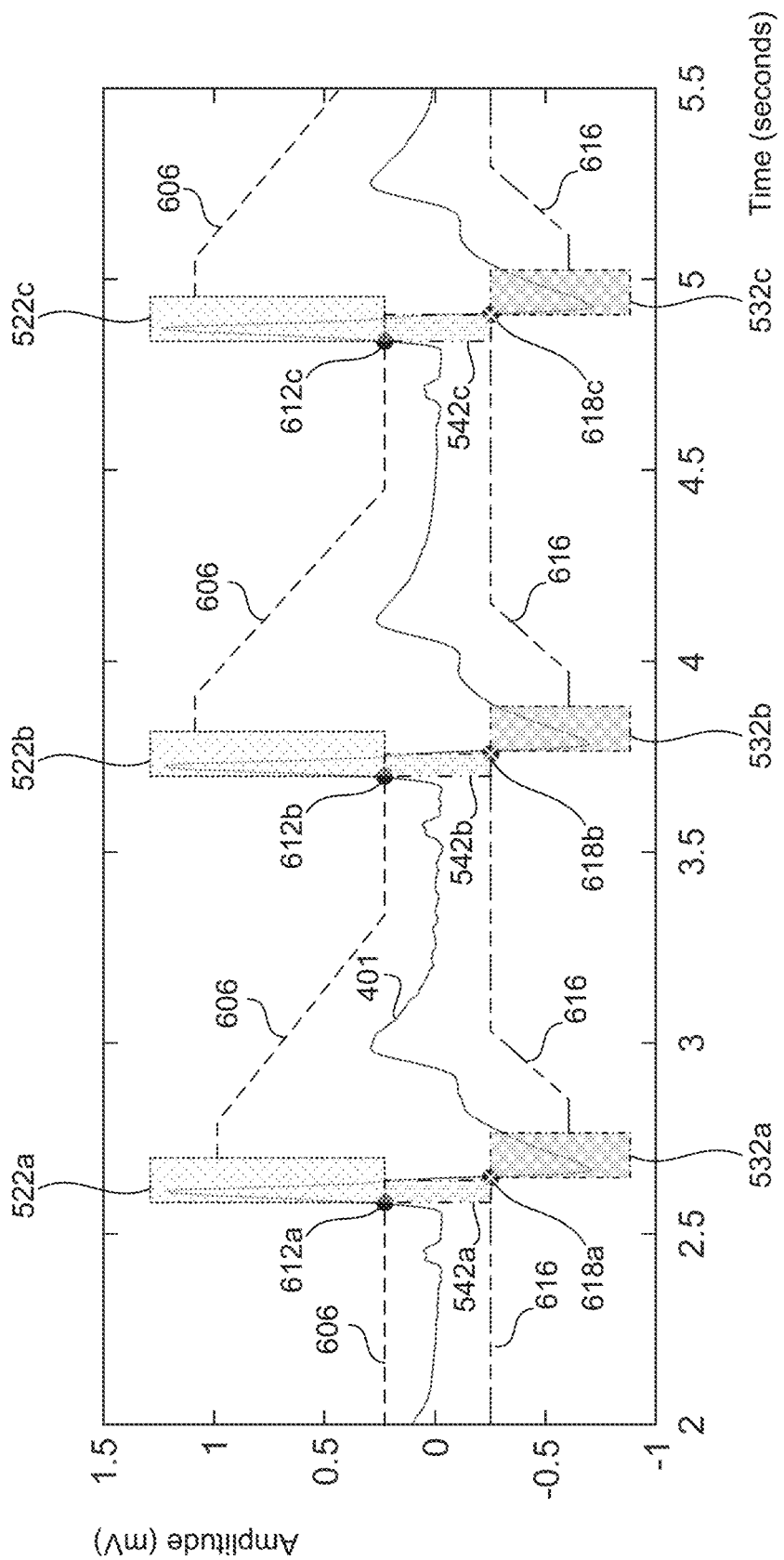
FIG. 6 illustrates the same far-field EGM signal during NSR shown in FIG. 4A, and is used to explain how first and second dynamic sensing thresholds can be used to detect ventricular sensed (VS) events in accordance with certain embodiments of the present technology, and to show how shared signal refractory periods can be used.

Referring now to FIG. 6, illustrated therein the same far-field EGM signal 401 during NSR shown in FIG. 4A, wherein the far-field EGM signal 401 is not rectified, and thus, can be referred to as a non-rectified far-field EGM signal. Also shown in FIG. 6 is a first dynamic sensing threshold 606 and a second dynamic sensing threshold 616.

The first dynamic sensing threshold 606 can be the same as or similar to the dynamic sensing threshold 506, in that the amplitude of the first dynamic sensing threshold following a sense refractory period is set to a specified percentage (e.g., 62.5 percent) of the peak of the far-field EGM signal 401 that was detected within the sense refractory period, remains at that amplitude for a decay delay period (e.g., 1.6 msec), and then decays at a decay rate (e.g., of 1 mV/sec) until reaching a specified minimum (e.g., a maximum sensitivity level).

Still referring to FIG. 6, the threshold crossings of the first dynamic sensing threshold 606 are labeled 612*a*, 612*b*, and 612*c*, and are each indicative of a detected potential VS event. FIG. 6 also includes refractory periods 522*a*, 522*b*, and 522*c*, which can also be referred to as positive signal refractory periods 522*a*, 522*b*, and 522*c*, since they are started in response to a positive portion of the non-rectified far-field EGM signal 401 crossing the first dynamic sensing threshold 606. The positive signal refractory periods 522*a*, 522*b*, and 522*c* can be referred to collectively as the positive signal refractory periods 522, or individually as a positive signal refractory period 522. In FIG. 6, the positive signal refractory periods 522*a*, 522*b*, 522*c* are started, respectively, in response to the threshold crossings 612*a*, 612*b*, and 612*c* of the first dynamic sensing threshold 606. Each of the positive signal refractory periods 522, after being started, ends (aka terminates or times-out) after a programmed first specified interval (e.g., 160 msec).

Also shown in FIG. 6 are refractory periods 532*a*, 532*b*, and 532*c*, which can also be referred to as negative signal refractory periods 532*a*, 532*b*, and 532*c*, since they are started in response to a negative portion of the non-rectified far-field EGM signal 401 crossing the second dynamic sensing threshold 616. The negative signal refractory periods 532*a*, 532*b*, and 532*c* can be referred to collectively as the negative signal refractory periods 532, or individually as a negative signal refractory period 532. In FIG. 6, the negative signal refractory periods 532*a*, 532*b*, 532*c* are started, respectively, in response to the threshold crossings 618*a*, 618*b*, and 618*c* of the second dynamic sensing threshold 616. Each of the negative signal refractory periods 532, after being started, ends (aka terminates or times-out) after a programmed second specified interval (e.g., 160 msec), which can be the same as the first specified interval mentioned above, but that need not be the case.

Also shown in FIG. 6 are shared signal refractory periods 542*a*, 542*b*, and 542*c*, which can be referred to collectively as the shared signal refractory periods 542, or individually as a shared signal refractory period 542. A shared signal refractory period 542 is started whenever the non-rectified far-field EGM signal 401 crosses the first dynamic sensing threshold 606 outside of both a positive signal refractory period 522 and a shared signal refractory period 542. While not specifically shown in FIG. 6 (but will be shown in FIG. 7, discussed below), a shared signal refractory period 542 is also started whenever the non-rectified far-field EGM signal 401 crosses the second dynamic sensing threshold 616 outside of both a negative signal refractory period 532 and a shared signal refractory period 542. In other words, each of the shared signal refractory periods is started in response to each crossing of the first dynamic sensing threshold 606 (aka each first threshold crossing) that occurs outside of the positive and the shared signal refractory periods, and each crossing of the second dynamic sensing threshold 616 (aka each second threshold crossing) that occurs outside of the negative and the shared signal refractory periods. Once a shared signal refractory period 542 is started in response to a positive portion the non-rectified far-field EGM signal 401 crossing the first dynamic sensing threshold 606, the shared signal refractory period 542 is ended in response to a negative portion of the non-rectified far-field EGM signal 401 crossing the second dynamic sensing threshold 616 or after a third specified interval, whichever occurs first. Conversely, if a shared signal refractory period 542 is started in response to a negative portion the non-rectified far-field EGM signal 401 crossing the second dynamic sensing threshold 616, the shared signal refractory period 542 is ended in response to a positive portion of the non-rectified far-field EGM signal 401 crossing the first dynamic sensing threshold 606 or after the third specified interval, whichever occurs first. More generally, a shared signal refractory period is started in response to each first threshold crossing that occurs outside of the positive and the shared signal refractory periods, and each said second threshold crossing that occurs outside of the negative and the shared signal refractory periods, and the shared signal refractory period is ended after the third specified interval or in response to the other one of the first or second threshold crossings occurring within the third specified interval. The third specified interval is greater than each of the first and second specified intervals (associated with the positive and negative signal refractory period) mentioned above. In other words, the maximum duration of each shared signal refractory period 542 is greater than the duration of each of the positive and negative signal refractory periods, e.g., the maximum duration of each shared signal refractory period 542 is 1.5 or 2 times the duration of each positive and negative signal refractory period.

In accordance with certain embodiments, each detected potential VS event that was detected within one of the shared signal refractory periods 542 is rejected, so as to avoid double counting of R-waves, or more generally, to avoid double counting of VS events. For example, since the detected potential VS events 618*a*, 618*b*, and 618*c* occur within the shared signal refractory periods 542*a*, 542*b*, and 542*c*, respectively (and cause the shared signal refractory periods 542*a*, 542*b*, and 542*c*, respectively, to end), they are rejected. This is why there is a small X in each of the dots labeled 618*a*, 618*b*, and 618*c*, to show that those detected potential VS events 618*a*, 618*b*, and 618*c* are rejected.

In the description herein, a threshold crossing or detected potential VS event is considered to occur within the shared signal refractory period when it causes the shared signal refractory period to end, as is the cases with the detected potential VS events 618*a*, 618*b*, and 618*c* shown in FIG. 6. By contrast, a threshold crossing or detected potential VS event that causes a shared signal refractory period to start is not considered to occur within the shared signal refractory period. Similarly, a first threshold crossing or detected potential VS event that causes a positive signal refractory period to start is not considered to occur within the positive signal refractory period, and a second threshold crossing or detected potential VS event that causes a negative signal refractory period to start is not considered to occur within the negative signal refractory period.

Figure 7:
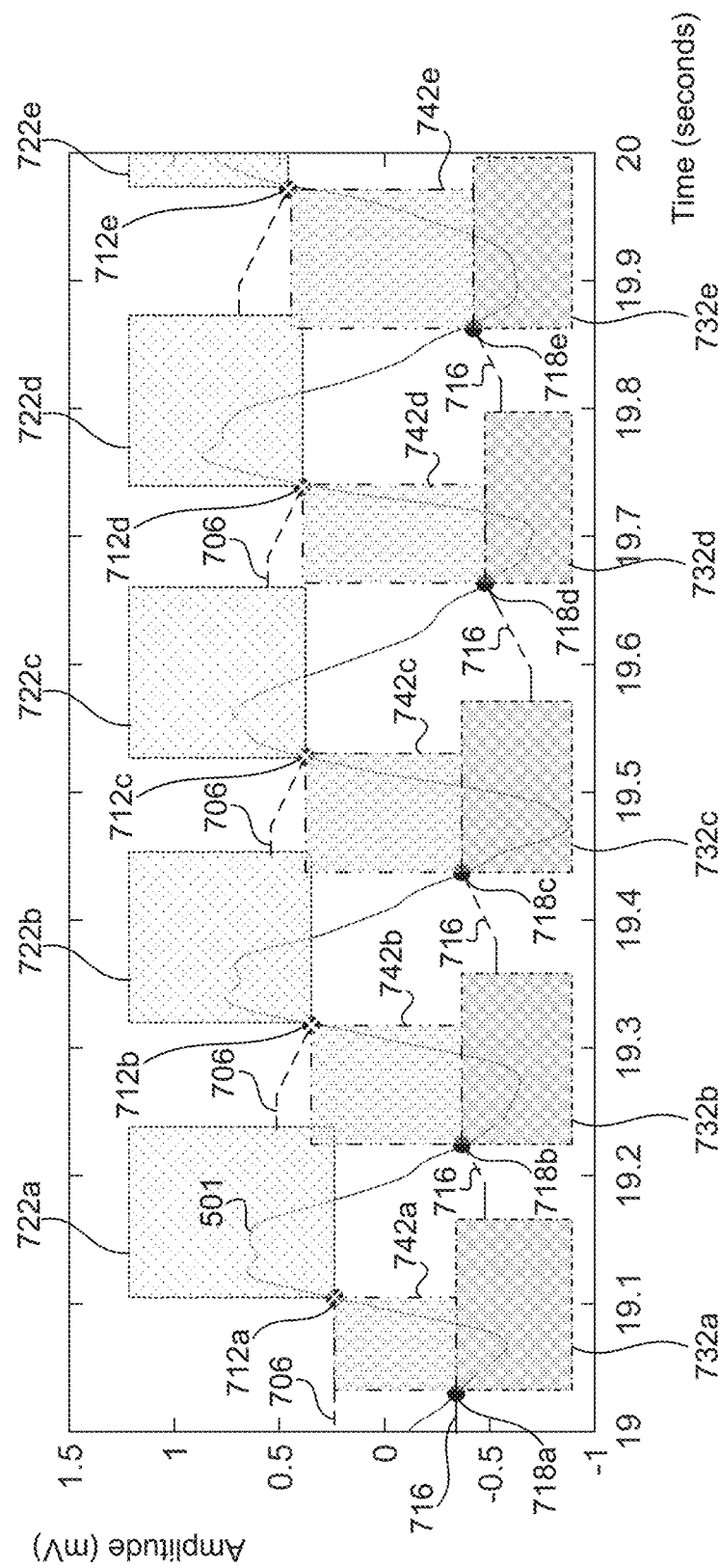
FIG. 7 illustrates the same far-field EGM signal during VF shown in FIG. 5A, and is used to explain how first and second dynamic sensing thresholds can be used to detect VS events in accordance with certain embodiments of the present technology, and to show how shared signal refractory periods can be used to avoid doubling counting or otherwise oversensing VS events.

Referring now to FIG. 7, illustrated therein the same far-field EGM signal 501 during VF shown in FIG. 5A, wherein the far-field EGM signal 501 is not rectified, and thus, can be referred to as a non-rectified far-field EGM signal. Also shown in FIG. 7 is a first dynamic sensing threshold 706 and a second dynamic sensing threshold 716. The first dynamic sensing threshold 706 can be the same as or similar to the dynamic sensing thresholds 506 and 606, in that the amplitude of the first dynamic sensing threshold following a sense refractory period is set to a specified percentage (e.g., 62.5 percent) of the peak of the far-field EGM signal that was detected within the sense refractory period, remains at that amplitude for a decay delay period (e.g., 1.6 msec), and then decays at a decay rate (e.g., of 1 mV/sec) until reaching a specified minimum (e.g., a maximum sensitivity level).

Still referring to FIG. 7, the threshold crossings of the first dynamic sensing threshold 706 are labeled 712a, 712b, 712c, 712d and 712e and are each indicative of a detected potential VS event. FIG. 7 also includes positive signal refractory periods 722a, 722b, 722c, 722d and 722e, that started in response to a positive portion of the non-rectified far-field EGM signal 501 crossing the first dynamic sensing threshold 706, and more specifically in response to the threshold crossings 712a, 712b, 712c, 712d and 712e, respectively, of the first dynamic sensing threshold 706. Each of the positive signal refractory periods 722, after being started, ends (aka terminates or times-out) after a programmed first specified interval (e.g., 160 msec).

Also shown in FIG. 7 are negative signal refractory periods 732a, 732b, 732c, 732d and 732e, started in response to a negative portion of the non-rectified far-field EGM signal 501 crossing the second dynamic sensing threshold 716. The negative signal refractory periods can be referred to collectively as the negative signal refractory periods 732, or individually as a negative signal refractory period 732. In FIG. 7, the negative signal refractory periods 732a, 732b, 732c, 732d and 732e are started, respectively, in response to the threshold crossings 718a, 718b, 718c, 718d and 718e of the second dynamic sensing threshold 716. Each of the negative signal refractory periods 732, after being started, ends (aka terminates or times-out) after a programmed second specified interval (e.g., 160 msec), which preferably has the same duration as the first specified interval mentioned above, but that need not be the case.

Also shown in FIG. 7 are shared signal refractory periods 742a, 742b, 742c, 742d and 742e, which can be referred to collectively as the shared signal refractory periods 742, or individually as a shared signal refractory period 742. The shared signal refractory period 742a is started in response to the threshold crossing 718a (which can also be referred to as the detected potential VS event 718a) and is ended in response to the threshold crossing 712a (which can also be referred to as the detected potential VS event 712a). The shared signal refractory period 742b is started in response to the threshold crossing 718b (which can also be referred to as the detected potential VS event 718b) and is ended in response to the threshold crossing 712b (which can also be referred to as the detected potential VS event 712b). The shared signal refractory period 742c is started in response to the threshold crossing 718c (which can also be referred to as the detected potential VS event 718c) and is ended in response to the threshold crossing 712c (which can also be referred to as the detected potential VS event 712c). The shared signal refractory period 742d is started in response to the threshold crossing 718d (which can also be referred to as the detected potential VS event 718d) and is ended in response to the threshold crossing 712d (which can also be referred to as the detected potential VS event 712d). The shared signal refractory period 742e is started in response to the threshold crossing 718e (which can also be referred to as the detected potential VS event 718e) and is ended in response to the threshold crossing 712e (which can also be referred to as the detected potential VS event 712e). The detected potential VS events 712a, 712b, 712c, 712d and 712e occur within the shared signal refractory periods 742a, 742b, 742c, 742d and 742e, respectively (and cause the shared signal refractory periods 742a, 742b, 742c, 742d and 742e, respectively, to end), and thus, they are rejected, which is why there is a small X in each of the dots labeled 712a, 712b, 712c, 712d and 712e.

In FIG. 7, the second dynamic sensing threshold 716 is a negative dynamic sensing threshold that is compared to negative portions of the same non-rectified far-field EGM signal 501 to which positive portions are compared to the first dynamic sensing threshold 706. Another equivalent way of comparing negative portions of the non-rectified far-field EGM signal 501 to the second dynamic sensing threshold 716 is to invert the non-rectified far-field EGM signal 501, to produce an inverted non-rectified far-field EGM signal 501' (shown in FIG. 8), and then compare the inverted non-rectified far-field EGM signal 501' to a positive second dynamic sensing threshold 716' (which is an inverted version of the dynamic sensing threshold 716') to detect second threshold crossings. This is shown in FIG. 8, which is discussed below.

Figure 8:
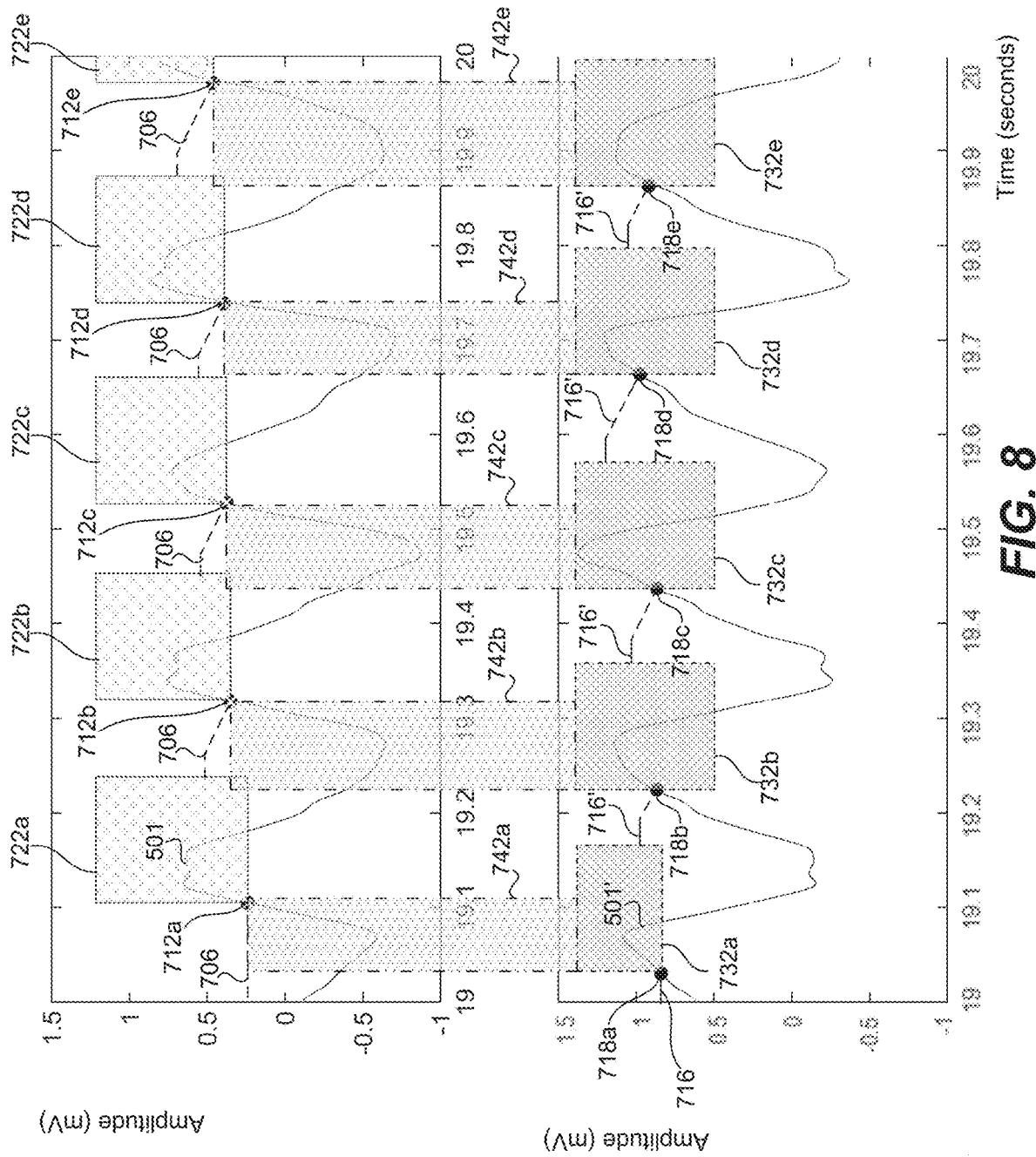
FIG. 8 illustrates how an inverted version of a far-field EGM signal can be used to detect second threshold crossings.

Referring now to FIG. 8, shown at the top is the same non-rectified far-field EGM signal 501 during VF shown in FIGS. 5A and 7. Also shown in FIG. 8, at the bottom, is the inverted non-rectified far-field EGM signal 501', which is an inverted version of the non-rectified far-field EGM signal 501. In FIG. 8, the second dynamic sensing threshold 716' is an inverted version of the second dynamic sensing threshold 716 shown in FIG. 7. Still referring to FIG. 8, the threshold crossings of the first dynamic sensing threshold 706 are labeled 712a, 712b, 712c, 712d and 712e and are each indicative of a detected potential VS event, and the threshold crossings of the second dynamic sensing threshold 716' are labeled 712a, 712b, 712c, 712d and 712e and are each indicative of a detected potential VS event. FIG. 8 also includes positive signal refractory periods 722a, 722b, 722c, 722d and 722e that are started in response to the first threshold crossings 712a, 712b, 712c, 712d and 712e, respectively, and each of which ends (aka terminates or times-out) after the programmed first specified interval (e.g., 160 msec). FIG. 8 also includes negative signal refractory periods 732a, 732b, 732c, 732d and 732e that are started in response to the second threshold crossings 718a, 718b, 718c, 718d and 718e, respectively, and each of which ends (aka terminates or times-out) after the programmed second specified interval (e.g., 160 msec). Also shown in FIG. 8 are the shared signal refractory periods 742a, 742b, 742c, 742d and 742e. The detected potential VS events 712a, 712b, 712c, 712d and 712e occur within the shared signal refractory periods 742a, 742b, 742c, 742d and 742e, respectively (and cause the shared signal refractory periods 742a, 742b, 742c, 742d and 742e, respectively, to end), and thus, they are rejected, which is why there is a small X in each of the dots labeled 712a, 712b, 712c, 712d and 712e.

Figure 9:
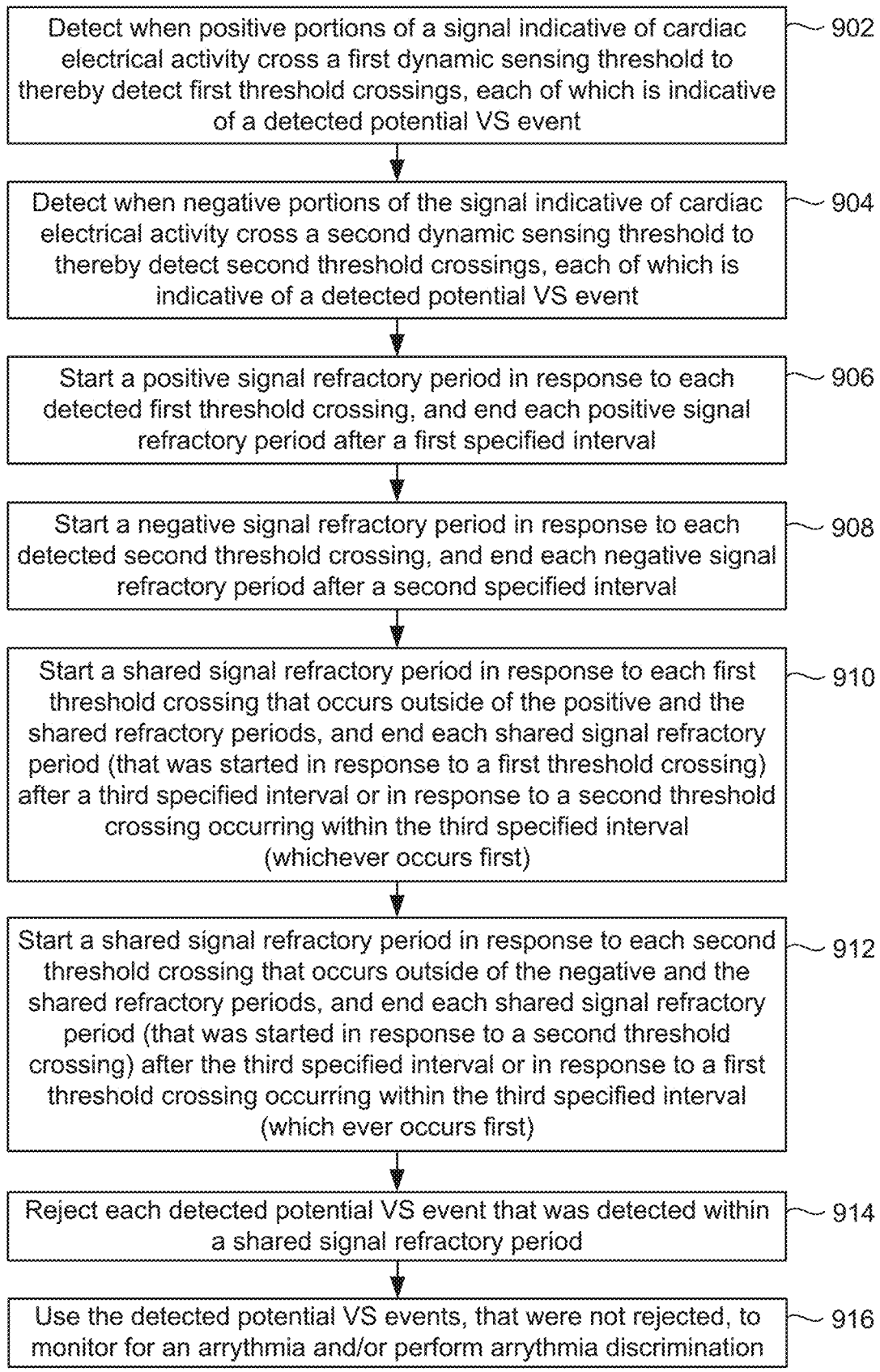
FIG. 9 is a high level flow diagram used to summarize embodiments of the present technology that can be used to accurately and robustly identify VS events from a signal indicative of cardiac electrical activity, such as a far-field EGM or ECG signal, and can be used to monitor for an arrythmia and/or perform arrythmia discrimination based on the VS events.

The high level flow diagram of FIG. 9 will now be used to summarize embodiments of the present technology that can be used to accurately and robustly identify VS events from a signal indicative of cardiac electrical activity, such as a far-field EGM or ECG signal, and can be used to monitor for an arrythmia and/or performing arrythmia discrimination based on the VS events. More generally, such embodiments can be used to reduce the chance of oversensing of VS events. Referring to FIG. 9, step 902 involves detecting when positive portions of the signal indicative of cardiac electrical activity cross a first dynamic sensing threshold to thereby detect first threshold crossings, each of which is indicative of a detected potential VS event. Step 904 involves detecting when negative portions of the signal indicative of cardiac electrical activity cross a second dynamic sensing threshold to thereby detect second threshold crossings, each of which is indicative of a detected potential VS event. The order of steps 902 and 904 can be reversed, or steps 902 and 904 can be performed at the same time. Referring briefly back to FIGS. 7 and 8, examples of the first threshold crossings are labelled 712a, 712b, 712c, 712d and 712e, and examples of the second threshold crossings are labeled 718a, 718b, 718c, 718d and 718e. In accordance with certain embodiments, steps 902 and 904 (and the other steps in FIG. 9) are performed in the digital domain, after a sensed far-field EGM/ECG signal is converted to a digital signal. It is also possible that the sensed far-field EGM/ECG signal is amplified and/or filtered prior to steps 902 and 904 being performed.

Referring again to FIG. 9, step 906 involves starting a positive signal refractory period in response to each detected first threshold crossing, and ending each said positive signal refractory period after a first specified interval. Step 908 involves starting a negative signal refractory period in response to each detected second threshold crossing, and ending each negative signal refractory period after a second specified interval, which is likely the same as the first specified interval. The order of steps 906 and 908 can be reversed, or steps 906 and 908 can be performed at the same time. Referring briefly back to FIGS. 7 and 8, examples of the positive signal refractory periods are labeled 722a, 722b, 722c, 722d and 722e, and examples the negative signal refractory periods are labeled 732a, 732b, 732c, 732d and 732e.

Referring again to FIG. 9, step 910 involves starting a shared signal refractory period in response to each first threshold crossing that occurs outside of the positive and the shared refractory periods, and ending each such shared signal refractory period (that was started in response to a first threshold crossing) after a third specified interval or in response to a second threshold crossing occurring within the third specified interval (whichever occurs first). Step 912 involves starting a shared signal refractory period in response to each second threshold crossing that occurs outside of the negative and the shared refractory periods, and ending each such shared signal refractory period (that was started in response to a second threshold crossing) after the third specified interval or in response to a first threshold crossing occurring within the third specified interval (whichever occurs first). Referring briefly back to FIGS. 7 and 8, examples of the shared signal refractory periods are labeled 742a, 742b, 742c, 742d and 742e. In FIGS. 7 and 8, the shared signal refractory period 742a is started in response to the second threshold crossing 718a and is ended in response to the first threshold crossing 712a; the shared signal refractory period 742b is started in response to the second threshold crossing 718b and is ended in response to the first threshold crossing 712b; the shared signal refractory period 742c is started in response to the second threshold crossing 718c and is ended in response to the first threshold crossing 712c; the shared signal refractory period 742d is started in response to the second threshold crossing 718d and is ended in response to the first threshold crossing 712d; and the shared signal refractory period 742e is started in response to the second threshold crossing 718e and is ended in response to the first threshold crossing 712e. Assuming for example that the third interval was programmed to be 200 msec, and FIGS. 7 and 8 showed a duration between the second threshold crossing 718a and the first threshold crossing 712a that was greater than the third interval (e.g., greater than 200 msec), then the shared signal refractory period 742a (that was started in response to the second threshold crossing 718b) would end after the third interval (e.g., 200 msec), rather than ending in response to the second threshold crossing 718b.

Referring again to FIG. 9, step 914 involves rejecting each detected potential VS event that was detected within a shared signal refractory period. In other words, each potential VS event that was detected within a shared signal refractory period (and caused the shared signal refractory period to end) is classified as an over-sensed VS event. As noted above, a threshold crossing or detected potential VS event is considered to occur within the shared signal refractory period when it causes the shared signal refractory period to end. Still referring to FIG. 9, step 916 involves using the detected potential VS events, that were not rejected, to monitor for an arrythmia and/or perform arrythmia discrimination. Step 916 can more specifically include monitoring for a ventricular arrhythmia based on a rate of the detected potential VS events that were not rejected, monitoring for a ventricular arrhythmia based on durations of intervals between the detected potential VS events that were not rejected, monitoring for a ventricular arrhythmia based on a variability of intervals between the detected potential VS events that were not rejected, and/or discriminating between VT and VF based on the detected potential VS events that were not rejected, but is not limited thereto. Examples of arrhythmias that can be monitored for and/or discriminated at step 916 include, but are not limited to VT and VF. Referring briefly back to FIGS. 7 and 8, the detected potential VS events 712a, 712b, 712c, 712d and 712e are examples of detected potential VS events that are rejected at step 914, and the detected potential VS events 718a, 718b, 718c, 718d and 718e that were not rejected are examples of detected potential VS events that are used to monitor for an arrythmia and/or perform arrythmia discrimination at step 916.

The steps described with reference to FIG. 9 can be performed by hardware, software, firmware, or any combination thereof, and more specifically can be performed by one or more processor, such as a programmable microcontroller (e.g., 1020 in FIG. 10). The embodiments of the present technology described herein beneficially reduce the probability of double-counting of R-wave, or more generally, of R-wave oversensing, and thereby provide for improved arrythmia detection and arrythmia discrimination. Explained another way, embodiments described herein can be used to reduce the chance of oversensing of VS events. Such embodiment can be implemented by an IMD. An example of such an IMD that can implement embodiments of the present technology, which were described above, is described below with reference to FIG. 10.

Example IMD

Figure 10:
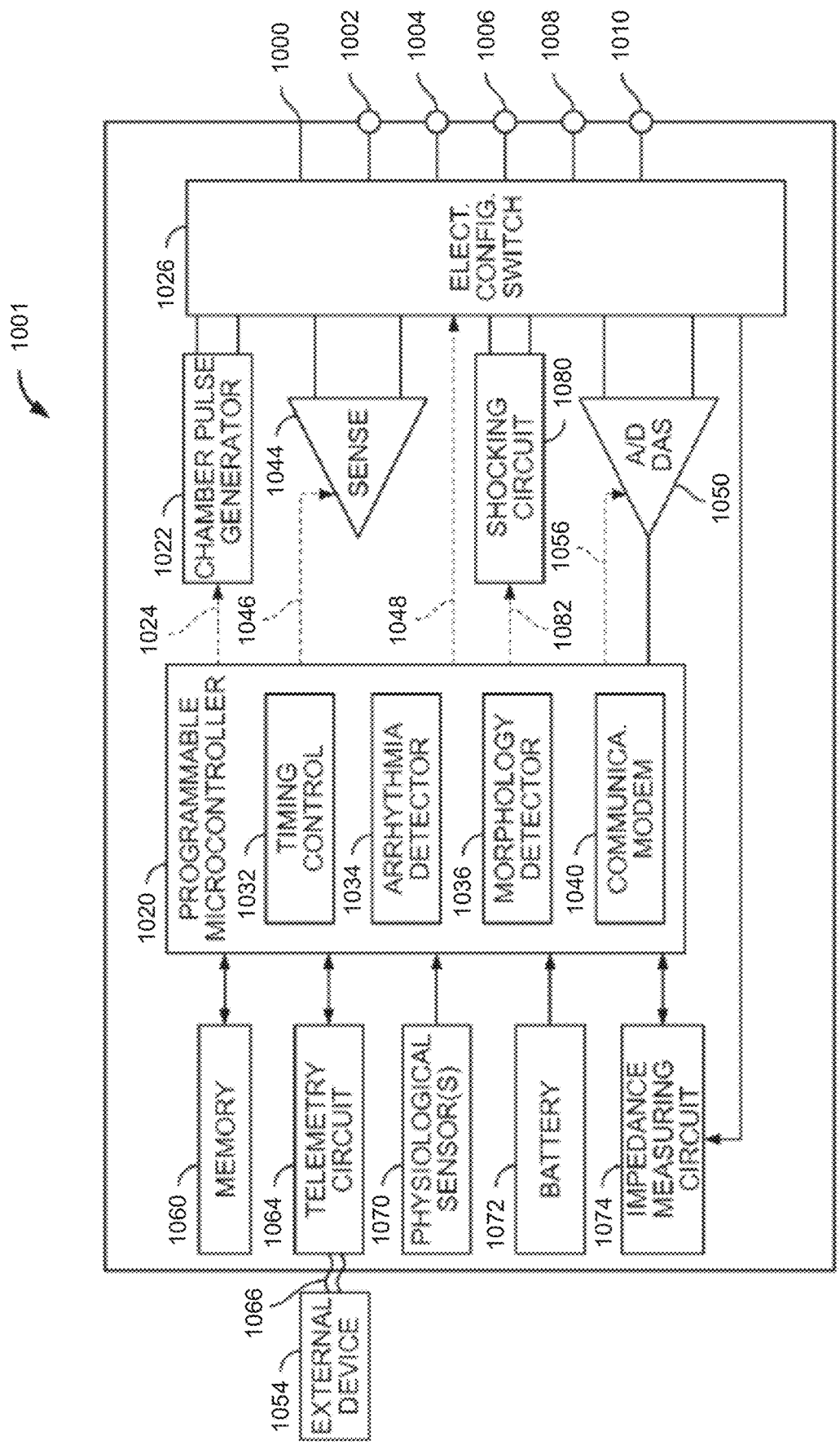
FIG. 10 is a high level block diagram of an example IMD that can implement certain embodiments of the present technology.

FIG. 10 shows a block diagram of one embodiment of an IMD (e.g., a pacemaker or ICD) 1001 that is implanted into a patient and can implement embodiments of the present technology described above. The IMD 1001 may be implemented as a full-function biventricular pacemaker, equipped with both atrial and ventricular sensing and pacing circuitry for four chamber sensing and stimulation therapy (including both pacing and shock treatment). Optionally, the IMD 1001 may provide full-function cardiac resynchronization therapy. Alternatively, the IMD 1001 may be implemented with a reduced set of functions and components. For instance, the IMD may be implemented without ventricular sensing and pacing. Indeed, the IMD can be an ICM that performs monitoring but not therapy.

The IMD 1001 has a housing 1000 to hold the electronic/computing components. Housing 1000 (which is often referred to as the "can", "case", "encasing", or "case electrode") may be programmably selected to act as the return electrode for certain stimulus modes. Housing 1000 may further include a connector (not shown) with a plurality of terminals 1002, 1004, 1006, 1008, and 1010. The terminals may be connected to electrodes that are located in various locations on housing 1000 or elsewhere within and about the heart. The IMD 1001 includes a programmable microcontroller 1020 that controls various operations of IMD 1001, including cardiac monitoring and stimulation therapy. Microcontroller 1020 includes a microprocessor (or equivalent control circuitry), RAM and/or ROM memory, logic and timing circuitry, state machine circuitry, and I/O circuitry.

IMD 1001 further includes a pulse generator 1022 that generates stimulation pulses for delivery by one or more electrodes coupled thereto. Pulse generator 1022 is controlled by microcontroller 1020 via control signal 1024. Pulse generator 1022 may be coupled to the select electrode(s) via an electrode configuration switch 1026, which includes multiple switches for connecting the desired electrodes to the appropriate I/O circuits, thereby facilitating electrode programmability. Switch 1026 is controlled by a control signal 1028 from microcontroller 1020.

In the embodiment of FIG. 10, a single pulse generator 1022 is illustrated. Optionally, the IMD may include multiple pulse generators, similar to pulse generator 1022, where each pulse generator is coupled to one or more electrodes and controlled by microcontroller 1020 to deliver select stimulus pulse(s) to the corresponding one or more electrodes.

Microcontroller 1020 is illustrated as including timing control circuitry 1032 to control the timing of the stimulation pulses (e.g., pacing rate, atrio-ventricular (AV) delay, atrial interconduction (A-A) delay, or ventricular interconduction (V-V) delay, etc.). Timing control circuitry 1032 may also be used for the timing of refractory periods, blanking intervals, noise detection windows, evoked response windows, alert intervals, marker channel timing, and so on. Microcontroller 1020 also has an arrhythmia detector 1034 for detecting arrhythmia conditions and a morphology detector 1036. Although not shown, the microcontroller 1020 may further include other dedicated circuitry and/or firmware/software components that assist in monitoring various conditions of the patient's heart and managing pacing therapies. Embodiment of the present technology described above with reference to FIGS. 6-9 can be implemented by the arrhythmia detector 1034. Other options are also possible.

The IMD 1001 is further equipped with a communication modem (modulator/demodulator) 1040 to enable wireless communication with an external device (e.g., 854), and/or with another implantable device, using radio frequency (RF) communication, inductive communication, or conductive communication, but not limited thereto. Modem 1040 may be implemented in hardware as part of microcontroller 1020, or as software/firmware instructions programmed into and executed by microcontroller 1020. Alternatively, modem 1040 may reside separately from the microcontroller as a standalone component. In certain embodiments, the modem 1040 includes both a conductive communication transceiver and an RF communication transceiver. While not specifically shown in FIG. 10, such an RF communication transceiver can be coupled to an antenna that enables RF communication signals to be transmitted and received for the purpose of transmitting and receiving messages to and from another IMD.

The IMD 1001 includes a sensing circuit 1044 selectively coupled to one or more electrodes, that perform sensing operations, through switch 1026 to detect the presence of cardiac activity in the right chambers of the heart. Sensing circuit 1044 may include dedicated sense amplifiers, multiplexed amplifiers, or shared amplifiers. It may further employ one or more low power, precision amplifiers with programmable gain and/or automatic gain control, bandpass filtering, and threshold detection circuit to selectively sense the cardiac signal of interest. The automatic gain control enables the unit to sense low amplitude signal characteristics of atrial fibrillation. Switch 1026 determines the sensing polarity of the cardiac signal by selectively closing the appropriate switches. In this way, the clinician may program the sensing polarity independent of the stimulation polarity.

The output of sensing circuit 1044 is connected to microcontroller 1020 which, in turn, triggers or inhibits the pulse generator 1022 in response to the presence or absence of cardiac activity. Sensing circuit 1044 receives a control signal 1046 from microcontroller 1020 for purposes of controlling the gain, threshold, polarization charge removal circuitry (not shown), and the timing of any blocking circuitry (not shown) coupled to the inputs of the sensing circuitry.

In the embodiment of FIG. 10, a single sensing circuit 1044 is illustrated. Optionally, the IMD may include multiple sensing circuits, similar to sensing circuit 1044, where each sensing circuit is coupled to one or more electrodes and controlled by microcontroller 1020 to sense electrical activity detected at the corresponding one or more electrodes. Sensing circuit 1044 may operate in a unipolar sensing configuration or in a bipolar sensing configuration.

IMD 1001 further includes an analog-to-digital (ADC) data acquisition system (DAS) 1050 coupled to one or more electrodes via switch 1026 to sample cardiac signals across any pair of desired electrodes. Data acquisition system 1050 is configured to acquire EGM or ECG signals, convert the raw analog data into digital data, and store the digital data for later processing and/or telemetric transmission to an external device 1054 (e.g., a programmer, local transceiver, or a diagnostic system analyzer). Data acquisition system 1050 is controlled by a control signal 1056 from the microcontroller 1020. The DAS 1050 can obtain the far-field EGM or ECG signals (e.g., 401 and 501) discussed above The microcontroller 1020 can be coupled to the memory 1060 by a suitable data/address bus. The programmable operating parameters used by microcontroller 1020 are stored in memory 1060 and used to customize the operation of the IMD 1001 to suit the needs of a particular patient. Such operating parameters define, for example, pacing pulse amplitude, pulse duration, electrode polarity, rate, sensitivity, automatic features, arrhythmia detection criteria, and the amplitude, waveshape and vector of each shocking pulse to be delivered to the patient's heart within each respective tier of therapy. The operating parameters of the IMD 1001 can also define the decay delay and the decay rate of the dynamic sensing thresholds (e.g., 606, 616, 706, 716, 716', etc.) and the maximum sensitivity level associated therewith. The operating parameters of the IMD 1001 can further define the various signal refractory periods described herein.

The operating parameters of the IMD 1001 may be non-invasively programmed into memory 1060 through a telemetry circuit 1064 in telemetric communication via communication link 1066 with external device 1054. Telemetry circuit 1064 allows intracardiac electrograms and status information relating to the operation of the IMD 1001 (as contained in microcontroller 1020 or memory 1060) to be sent to external device 1054 through communication link 1066.

IMD 1001 can further include magnet detection circuitry (not shown), coupled to microcontroller 1020, to detect when a magnet is placed over the unit. A magnet may be used by a clinician to perform various test functions of the IMD 1001 and/or to signal microcontroller 1020 that external device 1054 is in place to receive or transmit data to microcontroller 1020 through telemetry circuits 1064.

IMD 1001 can further include one or more physiological sensors 1070. Such sensors are commonly referred to as "rate-responsive" sensors because they are typically used to adjust pacing stimulation rates according to the exercise state of the patient. However, physiological sensor 1070 may further be used to detect changes in cardiac output, changes in the physiological condition of the heart, or diurnal changes in activity (e.g., detecting sleep and wake states). Signals generated by physiological sensors 1070 are passed to microcontroller 1020 for analysis. Microcontroller 1020 responds by adjusting the various pacing parameters (such as rate, AV Delay, V-V Delay, etc.) at which the atrial and ventricular pacing pulses are administered. While shown as being included within the IMD 1001, physiological sensor(s) 1070 may be external to the IMD 1001, yet still be implanted within or carried by the patient. Examples of physiologic sensors might include sensors that, for example, sense respiration rate, pH of blood, ventricular gradient, activity, position/posture, minute ventilation (MV), and so forth.

A battery 1072 provides operating power to all of the components in the IMD 1001. Battery 1072 is capable of operating at low current drains for long periods of time, and is capable of providing high-current pulses (for capacitor charging) when the patient requires a shock pulse (e.g., in excess of 2 A, at voltages above 2 V, for periods of 10 seconds or more). Battery 1072 also desirably has a predictable discharge characteristic so that elective replacement time can be detected. As one example, the IMD 1001 employs lithium/silver vanadium oxide batteries.

IMD 1001 further includes an impedance measuring circuit 1074, which can be used for many things, including: lead impedance surveillance during the acute and chronic phases for proper lead positioning or dislodgement; detecting operable electrodes and automatically switching to an operable pair if dislodgement occurs; measuring respiration or minute ventilation; measuring thoracic impedance for determining shock thresholds; detecting when the device has been implanted; measuring stroke volume; and detecting the opening of heart valves; and so forth. Impedance measuring circuit 1074 is coupled to switch 1026 so that any desired electrode may be used. In this embodiment the IMD 701 further includes a shocking circuit 1080 coupled to microcontroller 720 by a data/address bus 1082.

It is to be understood that the subject matter described herein is not limited in its application to the details of construction and the arrangement of components set forth in the description herein or illustrated in the drawings hereof. The subject matter described herein is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Further, it is noted that the term "based on" as used herein, unless stated otherwise, should be interpreted as meaning based at least in part on, meaning there can be one or more additional factors upon which a decision or the like is made. For example, if a decision is based on the results of a comparison, that decision can also be based on one or more other factors in addition to being based on results of the comparison.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the embodiments of the present technology without departing from its scope. While the dimensions, types of materials and coatings described herein are intended to define the parameters of the embodiments of the present technology, they are by no means limiting and are example embodiments. Many other embodiments will be apparent to those of skill in the art upon reviewing the above description. The scope of the embodiments of the present technology should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means—plus-function format and are not intended to be interpreted based on 35 U.S.C. § 112(f), unless and until such claim limitations expressly use the phrase "means for" followed by a statement of function void of further structure.

What is claimed is:

1. A method for identifying ventricular sensed (VS) events from a signal indicative of cardiac electrical activity, and monitoring for an arrythmia and/or performing arrythmia discrimination based on the VS events, the method comprising:
   (a) detecting when positive portions of the signal indicative of cardiac electrical activity cross a first dynamic sensing threshold to thereby detect first threshold crossings, each of which is indicative of a detected potential VS event;
   (b) detecting when negative portions of the signal indicative of cardiac electrical activity cross a second dynamic sensing threshold to thereby detect second threshold crossings, each of which is indicative of a detected potential VS event;
   (c) starting a positive signal refractory period in response to each said first threshold crossing, and ending each said positive signal refractory period after a first specified interval has elapsed;
   (d) starting a negative signal refractory period in response to each said second threshold crossing, and ending each said negative signal refractory period after a second specified interval has elapsed;
   (e) starting a shared signal refractory period in response to each said first threshold crossing that occurs outside of a previously started said positive signal refractory period that has not yet ended, if any, and outside of a previously started said shared signal refractory period that has not yet ended, if any;

(f) starting a shared signal refractory period in response to each said second threshold crossing that occurs outside of a previously started said negative signal refractory period that has not yet ended, if any, and outside of a previously started said shared signal refractory period that has not yet ended, if any;

(g) rejecting each said potential VS event detected within a said shared signal refractory period; and (h) using the detected potential VS events that were not rejected to monitor for an arrythmia or to perform arrythmia discrimination, or both.

2. The method of claim 1, wherein:

step (e) further comprises, for each said shared signal refractory period that is started in response to a said first threshold crossing, ending the shared signal refractory period after a third specified interval has elapsed or in response to a said second threshold crossing occurring, whichever occurs first; and step (f) further comprises, for each said shared signal refractory period that is started in response to a said second threshold crossing, ending the shared signal refractory period after the third specified interval has elapsed or in response to a said first threshold crossing occurring, whichever occurs first.

3. The method of claim 2, wherein:

the second specified interval has a same duration as the first specified interval; and the third specified interval has a greater duration than each of the first and the second specified intervals.

4. The method of claim 1, wherein the detecting when negative portions of the signal indicative of cardiac electrical activity cross the second dynamic sensing threshold at step (b) includes inverting the signal indicative of cardiac electrical activity to produce an inverted version of the signal indicative of cardiac electrical activity and comparing the inverted version of the signal indicative of cardiac electrical activity to the second dynamic sensing threshold to thereby detect second threshold crossings, each of which is indicative of a detected potential VS event.

5. The method of claim 1, further comprising separately adjusting the first dynamic sensing threshold and the second dynamic sensing threshold, such that the first dynamic sensing threshold is adjusted based on peaks in the signal indicative of cardiac electrical activity that are detected within the positive signal refractory periods, and the second dynamic sensing threshold is adjusted based on peaks in the signal indicative of cardiac electrical activity that are detected within the negative signal refractory periods.

6. The method of claim 5, wherein:

the adjusting the first dynamic sensing threshold includes
  setting a magnitude of the first dynamic sensing threshold, following a said positive signal refractory period, to a specified percent of a peak in the signal indicative of cardiac electrical activity that is detected within the positive signal refractory period; and
  after an optional decay delay period, gradually decreasing the magnitude of the first dynamic sensing threshold in accordance with a specified decay rate until the first dynamic sensing threshold reaches a specified minimum magnitude or another said first threshold crossing occurs, whichever occurs first; and the adjusting the second dynamic sensing threshold includes
  setting a magnitude of the second dynamic sensing threshold, following a said negative signal refractory period, to the specified percent of a peak in the signal indicative of cardiac electrical activity that is detected within the negative signal refractory period; and
  after the optional decay delay period, gradually decreasing the magnitude of the second dynamic sensing threshold in accordance with the specified decay rate until the second dynamic sensing threshold reaches the specified minimum magnitude or another said second threshold crossing occurs, whichever occurs first.

7. The method of claim 1, wherein the signal indicative of cardiac electrical activity comprises one of a non-rectified far-field electrogram (EGM) signal or a non-rectified far-field electrocardiogram (ECG) signal.

8. The method of claim 1, wherein the using the detected potential VS events, that were not rejected, to at least one of monitor for an arrythmia or perform arrythmia discrimination at step (h) comprises at least one of the following:

monitoring for a ventricular arrhythmia based on a rate of the detected potential VS events that were not rejected;

monitoring for a ventricular arrhythmia based on durations of intervals between the detected potential VS events that were not rejected;

monitoring for a ventricular arrhythmia based on a variability of intervals between the detected potential VS events that were not rejected; or discriminating between ventricular tachycardia (VT) and ventricular fibrillation (VF) based on the detected potential VS events that were not rejected.

9. An apparatus, comprising:

two or more electrodes;

a sensing circuit coupleable to at least two of the electrodes to thereby sense a signal indicative of cardiac electrical activity; and at least one processor configured to
  detect when positive portions of the signal indicative of cardiac electrical activity cross a first dynamic sensing threshold to thereby detect first threshold crossings, each of which is indicative of a detected potential VS event;
  detect when negative portions of the signal indicative of cardiac electrical activity cross a second dynamic sensing threshold to thereby detect second threshold crossings, each of which is indicative of a detected potential VS event;
  start a positive signal refractory period in response to each said first threshold crossing, and end each said positive signal refractory period after a first specified interval has elapsed;
  start a negative signal refractory period in response to each said second threshold crossing, and end each said negative signal refractory period after a second specified interval has elapsed;
  start a shared signal refractory period in response to each said first threshold crossing that occurs outside of a previously started said positive signal refractory period that has not yet ended, if any, and outside of a previously started said shared signal refractory period that has not yet ended, if any;
  start a shared signal refractory period in response to each said second threshold crossing that occurs outside of a previously started said negative signal refractory period that has not yet ended, if any, and outside of a previously started said shared signal refractory period that has not yet ended, if any;

reject each said potential VS event detected within a said shared signal refractory period; and use the detected potential VS events that were not rejected to monitor for an arrythmia or to perform arrythmia discrimination, or both.

10. The apparatus of claim 9, wherein the at least one processor is further configured to:

for each said shared signal refractory period that is started in response to a said first threshold crossing, end the shared signal refractory period after a third specified interval has elapsed or in response to a said second threshold crossing occurring, whichever occurs first; and for each said shared signal refractory period that is started in response to a said second threshold crossing, end the shared signal refractory period after the third specified interval has elapsed or in response to a said first threshold crossing occurring, whichever occurs first.

11. The apparatus of claim 10, wherein:

the second specified interval has a same duration as the first specified interval; and the third specified interval has a greater duration than each of the first and the second specified intervals.

12. The apparatus of claim 9, wherein the at least one processor is configured to detect when negative portions of the signal indicative of cardiac electrical activity cross the second dynamic sensing threshold by producing an inverted version of the signal indicative of cardiac electrical activity and comparing the inverted version of the signal indicative of cardiac electrical activity to the second dynamic sensing threshold to thereby detect second threshold crossings, each of which is indicative of a detected potential VS event.

13. The apparatus of claim 9, wherein the at least one processor is further configured to separately adjust the first dynamic sensing threshold and the second dynamic sensing threshold, such that the first dynamic sensing threshold is adjusted based on peaks in the signal indicative of cardiac electrical activity that are detected within the positive signal refractory periods, and the second dynamic sensing threshold is adjusted based on peaks in the signal indicative of cardiac electrical activity that are detected within the negative signal refractory periods.

14. The apparatus of claim 13, wherein the at least one processor is configured to:

adjust the first dynamic sensing threshold by setting a magnitude of the first dynamic sensing threshold, following a said positive signal refractory period, to a specified percent of a peak in the signal indicative of cardiac electrical activity that is detected within the positive signal refractory period; and after an optional decay delay period, gradually decreasing the magnitude of the first dynamic sensing threshold in accordance with a specified decay rate until the first dynamic sensing threshold reaches a specified minimum magnitude or another said first threshold crossing occurs, whichever occurs first; and adjust the second dynamic sensing threshold by setting a magnitude of the second dynamic sensing threshold, following a said negative signal refractory period, to the specified percent of a peak in the signal indicative of cardiac electrical activity that is detected within the negative signal refractory period; and after the optional decay delay period, gradually decreasing the magnitude of the second dynamic sensing threshold in accordance with the specified decay rate until the second dynamic sensing threshold reaches the specified minimum magnitude or another said second threshold crossing occurs, whichever occurs first.

15. The apparatus of claim 9, wherein the apparatus comprises an implantable medical device (IMD) and the signal indicative of cardiac electrical activity comprises one of a non-rectified far-field electrogram (EGM) signal or a non-rectified far-field electrocardiogram (ECG) signal.

16. The apparatus of claim 9, wherein the at least one processor is configured to at least one of:

monitor for a ventricular arrhythmia based on a rate of the detected potential VS events that were not rejected;

monitor for a ventricular arrhythmia based on durations of intervals between the detected potential VS events that were not rejected;

monitor for a ventricular arrhythmia based on a variability of intervals between the detected potential VS events that were not rejected; or discriminate between ventricular tachycardia (VT) and ventricular fibrillation (VF) based on the detected potential VS events that were not rejected.

17. A method, comprising:

comparing a non-rectified far-field electrogram (EGM) or electrocardiogram (ECG) signal to a first dynamic sensing threshold and to a second dynamic sensing threshold to thereby detect first threshold crossings and second threshold crossings, each of which is indicative of a detected potential ventricular sensed (VS) event;

initiating a positive signal refractory period in response to each said first threshold crossing, and initiating a negative signal refractory period in response to each said second threshold crossing;

initiating a shared signal refractory period in response to each said first threshold crossing that occurs outside of a previously started said positive signal refractory period that has not yet ended, if any, and outside of a previously started said shared signal refractory period that has not yet ended, if any;

initiating a shared signal refractory period in response to each said second threshold crossing that occurs outside of a previously started said negative signal refractory period that has not yet ended, if any, and outside of a previously started said shared signal refractory period that has not yet ended, if any; and monitoring for an arrythmia or performing arrythmia discrimination, or both, based on the detected potential VS events that were detected outside of the positive, the negative and the shared signal refractory periods.

18. The method of claim 17, wherein the comparing the non-rectified far-field EGM or ECG signal to the second dynamic sensing threshold includes inverting the non-rectified far-field EGM or ECG signal to produce an inverted version the non-rectified far-field EGM or ECG signal, which is compared to the second dynamic sensing threshold.

19. The method of claim 17, further comprising separately adjusting the first dynamic sensing threshold and the second dynamic sensing threshold.

20. The method of claim 17, further comprising:

for each signal refractory period of the positive and the negative signal refractory periods, ending the signal refractory period a specified duration after being initiated;

for each said shared signal refractory period initiated in response to a said first threshold crossing, ending the shared signal refractory period after a further specified interval has elapsed or in response to a said second threshold crossing occurring, whichever occurs first; and for each said shared signal refractory period initiated in response to a said second threshold crossing, ending the shared signal refractory period after the further specified interval has elapsed or in response to a said first threshold crossing occurring, whichever occurs first.

\* \* \* \* \*